US006869956B2

(12) United States Patent
Burke et al.

(10) Patent No.: US 6,869,956 B2
(45) Date of Patent: Mar. 22, 2005

(54) METHODS OF TREATING INFLAMMATORY AND IMMUNE DISEASES USING INHIBITORS OF IκB KINASE (IKK)

(75) Inventors: James R. Burke, Holland, PA (US); Robert M. Townsend, Boothwyn, PA (US); Yuping Qiu, Windsor, CT (US); Fred Christopher Zusi, Hamden, CT (US); Steven G. Nadler, Boothwyn, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/062,847

(22) Filed: Feb. 1, 2002

(65) Prior Publication Data

US 2003/0022898 A1 Jan. 30, 2003

Related U.S. Application Data

(63) Continuation-in-part of application No. 09/965,977, filed on Sep. 27, 2001.
(60) Provisional application No. 60/223,304, filed on Oct. 3, 2000, and provisional application No. 60/265,853, filed on Feb. 1, 2001.

(51) Int. Cl.[7] .......................... A61P 1/00; A61P 11/06; A61P 19/02; A61P 37/06; C07D 487/04
(52) U.S. Cl. ..................................................... 514/250
(58) Field of Search ........................ 514/256; 544/346

(56) References Cited

U.S. PATENT DOCUMENTS

| 4,160,097 A | 7/1979 | Warner, Jr. et al. ....... 548/343.5 |
| 4,172,947 A | 10/1979 | Warner, Jr. et al. ....... 548/343.5 |
| 4,191,766 A | 3/1980 | Warner, Jr. et al. ......... 514/250 |
| 4,191,767 A | 3/1980 | Warner, Jr. et al. ......... 514/250 |
| 4,198,508 A | 4/1980 | Warner, Jr. et al. ......... 544/346 |
| 4,200,750 A | 4/1980 | Warner, Jr. et al. ......... 544/346 |
| 4,225,724 A | 9/1980 | Warner, Jr. et al. ...... 514/343.5 |
| 4,229,452 A | 10/1980 | Warner, Jr. et al. ......... 514/250 |
| 4,236,015 A | 11/1980 | Warner, Jr. et al. ......... 435/194 |
| 5,153,196 A | 10/1992 | McQuaid et al. ............. 435/15 |
| 5,182,386 A | 1/1993 | Albaugh et al. ............ 435/194 |
| 5,196,421 A | 3/1993 | McQuaid et al. ........... 435/194 |
| 6,066,642 A * | 5/2000 | Jacobson et al. ........... 514/267 |
| 6,235,740 B1 | 5/2001 | Barrish et al. ............... 514/150 |

FOREIGN PATENT DOCUMENTS

| WO | WO 94/07893 | 4/1994 |
| WO | WO 97/17079 | 5/1997 |
| WO | WO 97/19079 | 5/1997 |
| WO | WO 98/48805 A1 * | 5/1998 |
| WO | WO 99/43704 | 9/1999 |
| WO | WO 01/58890 | 8/2001 |
| WO | WO 01/68648 | 9/2001 |

OTHER PUBLICATIONS

OneLook® Dictionary Search, [online] 2004, [retrieved on Mar. 15, 2004]. Retrieved from the internet, <http://onelook.com/?w=*&loc=revfp2&clue=%22inflammatory+lung+disease%22>.*
Platz J. and Bals R. Current Medicinal Chemistry—Anti–Inflammatory & Anti–Allergy Agents Mar. 2004, vol. 3, No. 1, pp. 39–52(14), abstract only.*
No Author, Trilateral Project B3b Theme: Comparative study on "reach–through claims" [online]. San Francisco, California, Nov. 5–9, 2001, [retrieved on Jun. 26, 2003]. Ret'd Internet <http://www.uspto.gov/web/tws/B3b_reach-through.pdf>.*
Arvin et al., Neuroscience and Biobehavioral Reviews, vol. 20 No. 3, pp. 445–452 (1996).
Dinarello, C.A., Journal of Biological Regulators and Homeostatic Agents, vol. 11 No. 3, pp. 91–103 (1997).
Baldwin, A., Annu. Rev. Immunol., vol. 14, pp. 649–681 (1996).
Christman, et al., Chest, vol. 117, pp. 1482–1487 (2000).
Siebenlist et al., Annu. Rev. Cell Biol., vol. 10, pp. 405–455 (1994).
Baeuerle et al., Cell, vol. 87, pp. 13–20 (1996).
Brown et al., Science, vol. 267, pp. 1485–1488 (1995).
Finco et al., Proc. Natl. Acad.Sci., vol. 91, pp. 11884–11888 (1994).
Baldi et al., The Journal of Biological Chemistry, vol. 271, pp. 376–379 (1996).
Roff et al., The Journal of Biological Chemistry, vol. 271, pp. 7844–7850 (1996).
Weil et al., The Journal of Biological Chemistry, vol. 272, pp. 9942–9949 (1997).
Whiteside et al., The EMBO Journal, vol. 16 No. 6, pp. 1413–1426 (1997).
Chen et al., Cell, vol. 84, pp. 853–862 (1996).
Lee et al., Cell, vol. 88, pp. 213–222 (1997).
DiDonato et al., Nature, vol. 388, pp. 548–554 (1997).
Zandi et al., Cell, vol. 91, pp. 243–252 (1997).
Mercurio et al., Science, vol. 278, pp. 860–866 (1997).
Woronicz et al., Science, vol. 278, pp. 866–870 (1997).
Li et al., The Journal of Biological Chemistry, vol. 273 No. 46, pp. 30736–30741 (1998).

(List continued on next page.)

Primary Examiner—Thomas C. McKenzie
(74) Attorney, Agent, or Firm—John A. Lamerdin; Audrey F. Sher

(57) ABSTRACT

The present invention describes methods of preventing and treating inflammatory and immune-related diseases or disorders using inhibitors of IκB kinase (IKK). Also described are IKK inhibitors effective for the prevention and treatment of inflammatory and immune-related diseases or disorders, as demonstrated in vivo. Further embodiments of the present invention relate to a specific IKK inhibitors, 4(2'-aminoethyl)amino-1,8-dimethylimidazo(1,2-a) quinoxaline and compounds of formula (I), salts thereof, and pharmaceutical compositions.

4 Claims, 3 Drawing Sheets

OTHER PUBLICATIONS

Regnier et al., Cell, vol. 90, pp. 373–383 (1997).
Ghoda et al., The Journal of Biological Chemistry, vol. 272 No. 34, pp. 21281–21288 (1997).
Peters et al., Molecular Cell, vol. 5, pp. 513–522 (2000).
Mallnin et al., Nature, vol. 385, pp. 540–544 (1997).
Song et al., Proc. Natl. Acad. Sci., vol. 94, pp. 9792–9796 (1997).
Karin et al., Annual Review of Immunology, vol. 18, pp. 621–663 (2000).
Yin et al., Nature, vol. 396, pp. 77–80 (1998).
Yan et al., The Journal of Biological Chemistry, vol. 274 No. 51, pp. 36631–36636 (1999).
Peskar et al., Digestive Diseases and Sciences, vol. 32 No. 12, pp. 51S–56S (1987).
Horn et al., Scand. J. Gastroenterol., vol. 26, pp. 867–869 (1991).
Yamamoto et al., The Journal of Biological Chemistry, vol. 274 No. 38, pp. 27307–27314 (1999).
Rossi et al., Nature, vol. 403, p. 103–108 (2000).
Kapahi et al., The Journal of Biological Chemistry, vol. 275 No. 46, pp. 36062–36066 (2000).
Colotta et al., Eur. J.Med.Chem., vol. 30, pp. 133–139 (1995).
Ceccarelli et al., Eur. J. Med.Chem., vol. 33, pp. 943–955 (1998).
Li et al., Science, vol. 284, pp. 321–325 (1999).
Hu et al., Science, vol. 284, pp. 316–320 (1999).
Mignani et al., Drug Development Research, vol. 48, pp. 121–129 (1999).
Damour et al., Heterocycles, vol. 50, No. 1, pp. 259–267 (1999).
Witkamp et al., The Veterinary Quarterly, vol. 22 No. 1, pp. 11–16 (2000).
Verma et al., Proc. Natl. Acad. Sci., vol. 94 pp. 11758–11760 (1997).

* cited by examiner

METHODS OF TREATING INFLAMMATORY AND IMMUNE DISEASES USING INHIBITORS OF IκB KINASE (IKK)

RELATED INVENTIONS

This application claims benefit to application U.S. Ser. No. 60/223,304, filed Oct. 3, 2000 and application U.S. Ser. No. 60/265,853, filed Feb. 1, 2001, and is a continuation-in-part of U.S. Ser. No. 09/965,977, filed Sep. 27, 2001. The contents of all of which are hereby incorporated by reference herein in their entireties.

FIELD OF THE INVENTION

The present invention relates to methods of using inhibitors of IκB kinase (IKK) in the treatment of inflammatory and immune diseases, to inhibitors of IKK, and to pharmaceutical compositions comprising such inhibitors, together with a pharmaceutically or physiologically-acceptable vehicle or excipient.

BACKGROUND OF THE INVENTION

Tumor necrosis factor (TNF-α) is a potent cytokine having pro-inflammatory properties that is released by many cell types when stimulated. Studies have shown a relationship between elevated levels of TNF-α and a variety of diseases including septic shock, hematopoiesis, tumors, and inflammatory disorders of the central nervous system including HIV, encephalitis, cerebral malaria, and meningitis. Neurodegenerative diseases such as Alzheimer's disease, Parkinson's disease, and Creutzfeldt-Jacob disease also are reportedly associated with enhanced TNF-α levels. See, e.g., Arvin et al., "The Role of Inflammation and Cytokines in Brain Injury," Neuroscience and Biobehavioral Reviews, Vol. 20, No. 3 (1996), at pp. 445–452. Accordingly, various classes of compounds have been researched and developed to inhibit TNF-α production at both transcriptional and translational levels, e.g., corticosteroids, rolipram (a phosphodiesterase IV inhibitor suppressing TNF-α mRNA synthesis), calphostin, and imidazole-type cytokine suppressing anti-inflammatory drugs (CSAIDs). See, e.g., Dinarello, "Role of Pro- and Anti-Inflammatory Cytokines During Inflammation: Experimental and Clinical Findings, Review, Vol. 0393-974X (1997), at pp. 91–103.

Recently, attention has focused on the role of nuclear factor-κB (NF-κB) in the activation pathway that leads to production of TNF-α and other inflammatory cytokines and gene types. Besides TNF-α, NF-κB modulates many genes involved in immune function and inflammation, including interleukin (IL)-2, IL-6, IL-8, IL-2Rα, GM-CSF, intercellular adhesion molecule (ICAM-1), and vascular cellular adhesion molecule-1 (VCAM-1). Thus, inhibition of NF-κB and/or its activation pathway provides a means for treating a wide range of diseases including autoimmune diseases, Alzheimer's disease, atherosclerosis, oncogenesis, and so forth. See, e.g., Baldwin, "The NF-κB and IκB Proteins: New Discoveries and Insights," Annual Rev. Immunol. Vol. 14 (1996), at pp. 649–81; see also Christman et al., "Impact of Basic Research on Tomorrow's Medicine, The Role of Nuclear Factor-κB in Pulmonary Diseases," Chest, Vol. 117 (2000), at pp. 1482–87.

NF-κB is a transcriptional activator, which plays a central role in regulating the transcription of a number of genes including those, which encode proteins, involved in inflammatory and immune responses. Representative examples of genes controlled by NF-κB include the cytokines tumor necrosis factor (TNF-α), IL-1β, IL-6, and IL-8; the adhesion molecules E-selectin and vascular cell adhesion molecule (VCAM)-1; and the enzyme nitric oxide (NO)-synthase (for reviews, see Siebenlist et al. Annu. Rev. Cell Biol. 10:405–455, 1994; Bauerle and Baltimore, Cell 87:13–20, 1997). Also, NF-κB has been shown to be inducible by several stimuli, in addition to mediators of immune function, such as UV irradiation, growth factors, and viral infection.

NF-κB transcription factor normally resides in the cytoplasm in unstimulated cells as an inactive complex with a member of the inhibitor κB (IκB) inhibitory protein family. The IκB class of proteins includes IκB-α, IκB-β, and IκB-ε all of which contain ankyrin repeats for complexing with NF-κB (for review, see Whiteside et al., EMBO J. 16:1413–1426, 1997). In the case of IκB-α, the most carefully studied member of this class, stimulation of cells with agents which activate NF-κB-dependent gene transcription results in the phosphorylation of IκB-α at serine-32 and serine-36 (Brown et al. Science, 267:1485–1488, 1995).

Potential inhibitors of NF-κB and/or the NF-κB pathway have been identified as including Interleukin-10, glucocorticoids, salicylates, nitric oxide, and other immunosuppressants. IκB is a cytoplasmic protein that controls NF-κB activity by retaining NF-κB in the cytoplasm. IκB is phosphorylated by the IκB kinase (IKK), which has two isoforms, IKK-1 (or IκB kinase α, IKKα) and IKK-2 (or IκB kinase β, IKKβ). Upon phosphorylation of IκB by IKK, NF-κB is rapidly released into the cell and translocates to the nucleus where it binds to the promoters of many genes and up-regulates the transcription of pro-inflammatory genes. Inhibitors of IKK can block the phosphorylation of IκB and further downstream effects, specifically those associated with NF-κB transcription factors. Glucocorticoids reportedly inhibit NF-κB activity by two mechanisms, i.e., upregulating IκB protein levels and inhibiting NF-κB subunits. Nitric oxide also reportedly inhibits NF-κB through upregulation of IκB. However, these mechanisms of interaction are complex; for example, production of nitric oxide in lymphocytes reportedly enhances NF-κB activity.

Phosphorylation of IκB-α is critical for its subsequent ubiquitination and proteolysis, upon which NF-κB is released from complexing with IκB. NF-κB can then translocate into the nucleus and ultimately, activate gene transcription (Finco et al., Proc. Natl. Acad. Sci. USA 91:11884–11888, 1994; Baldi et al. J. Biol. Chem. 271:376–379, 1996; Roff et al. J. Biol. Chem. 271:7844–7850, 1996). Substituting both serine-32 and serine-36 of IκB with alanine prevents signal-induced NF-κB activation and also results in an IκB (e.g. IκB-α), which is not phosphorylated, ubiquitinated, or proteolytically digested (Roff et al. J. Biol. Chem. 271:7844–7850, 1996). Analogous serines have been identified in both IκB-β and IκB-ε, and phosphorylation at these residues appears to regulate the proteolytic degradation of these proteins by a mechanism similar to that of IκB-α (Weil et al. J. Biol. Chem. 272:9942–9949, 1997; Whiteside et al. EMBO J. 16:1413–1426, 1997).

More particularly, upon phosphorylation, ubiquitination, and degradation of IκB, NF-κB is released from the IκB/NF-κB complex and allowed to translocate from the cytoplasm to the nucleus and activate a number of genes, particularly those involved in inflammatory and immune responses. Since NF-κB is of significant importance in inflammation and immune responses, inhibition of the signal-inducible phosphorylation of IκB can be an important target for novel anti-inflammatory and immune-related agents in the treatment of inflammatory and immune system-related diseases and disorders, as described herein.

IκB kinase (IKK) is a high molecular weight (500–900 kD) multisubunit enzyme which phosphorylates IκB-α at positions serine-32 and serine-36 and has been isolated from HeLa cells (Chen et al. Cell 84:853–862, 1996; Lee et al. Cell 88:213–222, 1997; DiDonato et al. Nature 388:548–554, 1997). Two catalytic subunits termed IKK-1 and IKK-2 of IKK have been identified, cloned, and demonstrated to be widely expressed in human tissues (DiDonato et al. Nature 388:548–554, 1997; Zandi et al. Cell 91:243–252, 1997; Mercurio et al. Science 278:860–866, 1997; Woronicz et al. Science 278:866–869, 1997; Li et al. J. Biol. Chem. 273:30736–30741, 1998; Regnier et al. Cell 90:373–383, 1997).

The IKK-1 and IKK-2 catalytic subunits of IKK are highly homologous, having 50% sequence identity and more than 70% sequence similarity. IKK-1 and IKK-2 are 85- and 87-kDa proteins, respectively. Both kinases contain a catalytic domain followed by a leucine zipper domain and a helix-loop-helix (HLH) domain (Mercurio et al. Science, 278:860–866, 1997). When one subunit is recombinantly expressed without the other subunit, either one is still able to catalyze the phosphorylation of IκB (Li et al. J. Biol. Chem., 273:30736–30741, 1998). Thus, IKK, either IKK-1 or IKK-2, can play an important role in signaling IκB for ubiquination and further degradation.

In addition, in vitro studies have demonstrated that the full length IKKβ can autophosphorylate and phosphorylate its substrate, IκBα, as well; however, neither the N-terminal kinase domain-containing form, nor the C-terminal HLH domain-containing form of IKK was capable of autophosphorylation (U.S. Pat. No. 6,077,701 to Chu et al.). U.S. Pat. No. 6,077,701 discloses that compounds which increase IKKβ activity and/or binding to IκB can be potential modulators of inflammatory disease.

Evidence that IKK is involved in the signal inducible degradation of IκB-α was provided by both anti-sense inhibition of IKK-1 and the use of dominant-negative, catalytically-inactive mutants of IKK-1 and IKK-2 (DiDonato et al. Nature 388:548–554, 1997; Mercurio et al. Science 278:860–866, 1997; Woronicz et al. Science 278:866–869, 1997). Both approaches abrogated cytokine- and lipopolysaccharide (LPS)-induced activation of NF-κB. These in vitro assays implicate a role for IKK in activating NF-κB.

There are other kinases which can phosphorylate IκB and which have been implicated in the activation of NF-κB. For example, two kinases (pp90rsk and IKK-ε) have been demonstrated to phosphorylate IκB-α at serine-32 and/or serine-36. The overexpression of these kinases, and the use of dominant negative mutants to these kinases, have indicated a role for them in the phosphorylation of IκB in cells (Ghoda et al., J. Biol. Chem. 272:21281–21288, 1997; Peters et al., Mol. Cell. 5:513–522, 2000). The existence of multiple IκB kinases is indicative of redundant signaling pathways. Therefore, it is possible that an inhibitor of IKK-1 and/or IKK-2 can not necessarily show anti-inflammatory or immunosuppressive effects due to redundant signaling pathways in at least some cells.

Several in vitro types of studies have been performed to further investigate IKK and its properties. The in vitro types of cell biology studies (for example, overexpression of either IKK-1 or IKK-2, or of dominant negative versions of these kinases (DiDonato et al. Nature 388:548–554, 1997; Mercurio et al. Science 278:860–866, 1997; Woronicz et al. Science 278:866–869, 1997; Regnier et al. Cell 90:373–383, 1997; Zandi et al. Cell 91:243–252, 1997)) that appear to implicate IKK-1 and IKK-2 in NF-κB activation are sometimes artifactual. A particular example of such an artifactual study involves a kinase known as NF-κB-inducing kinase, NIK.

Overexpression of NIK in cells activated IKK and NF-κB, while expression of kinase-inactive forms of the enzyme blocked the stimulated activation of IKK and NF-κB (Malinin et al., Nature 385:540–544, 1997; Song et al., Proc. Nat. Acad. Sci. USA 94:9792–9796, 1997). Based on the foregoing, as well as on yeast two-hybrid studies showing a strong interaction between NIK and IKK (Regnier et al., Cell 90:373–383, 1997), NIK is suggested to be essential for the activation of IKK and, subsequently, NF-κB.

Additional studies have demonstrated that the NIK-IKK protein-protein interaction is important for NF-κB-dependent responses (WO99/43704; Publication Date: Sept. 2, 1999; Goeddel et al., U.S. Pat. Nos.: 5,851,812; 5,916,760; and 5,939,302). Goeddel et al. show that transient IKKβ overexpression induces luciferase reporter gene activity in both HeLa and 293 cells and overexpression of kinase-inactive IKKβ, which still associates with NIK, blocks activation. However, it was further determined that cells derived from mice deficient in NIK had no abrogated NF-κB activation (Karin and Ben-Nariah, Ann. Rev. Immunol., 18:621–663, 2000). Therefore, although some studies suggest the importance of NIK as a potential target for inhibiting NF-κB activation, the experimental results were not demonstrable in vivo, as reported by Karin and Ben-Nariah (supra). Thus, it is very important that in vitro-based and strictly cell biology-based experiments using overexpressed proteins always be cautiously interpreted.

Although there are several known synthetic inhibitors of IKK, none of these have played a successful role in vivo in disease inhibition. For example, aspirin (acetylsalicyclic acid) and salicylate have been demonstrated to be inhibitors of IKK-1 and IKK-2, but only at high, non-physiological concentrations which are much higher than those required to block prostaglandin synthesis through the inhibition of cyclooxygenase (Yin et al., Nature 396:77–80, 1998). Therefore, these agents are inappropriate for use in treatments or for testing the role of IKK in disease.

Similar to aspirin, 5-aminosalicyclic acid has been shown to inhibit IKK (Yan and Polk, J. Biol. Chem. 274:36631–36636, 1999), but this compound has several other activities, including the inhibition of prostaglandin and leukotriene synthesis (Peskar et al., Deg. Disc. Sci., 32:51S–56S, 1987; Horn et al., Scand. J. Gastroenterol. 26:867–879, 1991) which thereby precludes its use in testing the role of IKK in disease.

Sulindac is a cyclooxygenase inhibitor that has been demonstrated to also inhibit IKK-2 (Yamamoto et al., J. Biol. Chem. 274:27307–27314, 1999). However, in studies similar to those using aspirin, the concentrations of sulindac necessary for inhibiting IKK were much greater than those needed to inhibit cyclooxygenase. Therefore, this agent is also inappropriate for testing the role of IKK in disease.

Other inhibitors of IKK, more specifically of IKK-2, are cyclopentenone prostaglandins, such as 15dPGJ2 (Rossi et al., Nature 403:103–108, 2000). However, 15dPGJ2, can also activate peroxisome proliferator-activated receptor-gamma (PPAR-γ), a nuclear receptor that interferes with NF-κB transcriptional activity. Therefore, any anti-inflammatory effect could be explained by PPAR-γ activity rather than IKK inhibition. Thus, this inhibitor is not specific for inhibiting the downstream effects of NF-κB-induced inflammation via IKK.

Arsenite, another IKK inhibitor, is a reactive environmental toxin that has been shown to inhibit both IKK-1 and IKK-2 (Kapahi et al., J. Biol. Chem., 275:36062–36066, 2000). Due to its toxic effects, the therapeutic benefits or in vivo treatment utility of arsenite would therefore preclude its use in patients.

U.S. Pat. Nos. 4,229,452 and 4,200,750 to Warner et al., Colotta et al. (Eur. J. Med. Chem. 30:133–139, 1995) and Ceccarelli et al. (Eur. J. Med. Chem. 33:943–955, 1998; WO97/17079; May 29, 1997) disclose compounds that are structurally different from compound 6 as described herein.

The Aventis Pharma Deutschland GMBH(WO 01/68648) publication discloses particular substituted beta-carboline compounds. The WO 01/68648 publication does not disclose the IKK inhibitor compound(s) of the present invention, which have been shown to function and have proven to be effective in a variety of in vivo animal models of diseases or pathologies associated with inflammation, e.g. animal models of arthritis, inflammatory bowel disease, and pulmonary inflammation, and graft survival.

The Astrazeneca AB (WO 01/58890) publication discloses particular heteroaromatic carboxamide derivatives that are structurally different from the compounds of the present invention. The compounds of the WO 01/58890 publication do not demonstrate in vivo efficacy of the IKK inhibitor compounds of the present invention in animal models of disease associated with inflammation and/or the immune system.

In animal models of disease (i.e. knock-out mice) designed to test inhibition of IKK, the deletion of IKK-1 or IKK-2 has been demonstrated to be embryonic lethal (Li et al. Science 284:321–325, 1999; Hu et al. Science 284:316–320, 1999). Therefore, the use of IKK knockout mice to demonstrate a role of IKK in disease is neither practical nor feasible. In contrast, the present invention demonstrates for the first time that inhibitors of the catalytic activity of IKK-1 and IKK-2 are effective in murine models of disease. Such models are believed to be predictive of similar effects in human patients. Therefore, the treatment methods, in vivo models, and effectiveness of IKK inhibitors as described herein, are extremely beneficial and advantageous for the advancement of discovering and employing therapeutics for inflammation and immune system diseases. These animal models are therefore important tools for studying human diseases, specifically inflammatory and immune-related diseases.

Lactam-based tetracyclic compounds useful as antagonists of NMDA(N-methyl-D-aspartate) and AMPA (α-3-hydroxy-5-methylisoxazole-4-propionate) receptors are disclosed in WO 94/07893, Preparation of 5H, 10H-imidazo [1,2-a]indeno[1,2-e]pyrazine-4-one AMPA/KA Receptor Antagonist, filed by Aloup et al; and in articles by Mignani, Aloup, et al., "Synthesis and Pharmacological Properties of 5H, 10H-imidazo[1,2-a]indeno[1,2-e]pyrazine-4-one, a New Competitive AMPA/KA Receptor Antagonist," Drug. Dev. Res., Vol. 48 (3) (1999), at pp. 121–29, and "An Efficient Preparative Route to Fused Imidazo[1,2-a]-Pyrazin-4-one Derivatives," Heterocycles, Vol. 50, No.1 (1999), at pp. 259–267. Compounds such as lactams that are claimed to be useful for blocking excitatory amino acid receptors found in the brain and spinal cord are shown in U.S. Pat. Nos. 5,153,196 and 5,196,421, both assigned to Eli Lilly and Company. Tricyclic compounds having amino-substituents claimed to be useful as brain receptor ligands are disclosed in U.S. Pat. No. 5,182,386, assigned to Neurogen Corp., and in U.S. Pat. Nos. 4,160,097; 4,172,947; 4,191,766; 4,191,767; 4,198,508; 4,200,750; 4,225,724; and 4,236,015 in WO97/19,079, and in S. Ceccarelli et al, "Imidazo[1,2-a]quinoxalin-4-amines: A Novel Class of Nonxanthine A1-Adenosine Receptor Antagonists," European Journal of Medicinal Chemistry Vol. 33, (1998), at pp. 943–955. To applicants' knowledge, 4-amino substituted tetracyclic compounds according to formula (I) have not been previously described.

As can be appreciated, those in the field of pharmaceutical research continue to seek to develop new compounds and compositions having increased effectiveness, bioavailability, and solubility, having fewer side effects, and/or providing the consumer with a choice of options. Particularly in the area of immune response, many individuals respond differently depending upon the type of treatment and chemical agent used. Mechanisms of action continue to be studied to aid in understanding the immune response and in developing compounds effective for treating immune-related disorders.

In view of the dearth of safe, effective, and novel therapeutics for treating inflammatory or immune-related diseases, there is a need for new anti-inflammatories and agents that reduce, eliminate, and/or ameliorate inflammation and immune-related disease. In addition, the discovery of additional proteins involved in the processes of inflammation and immune-related diseases and disorders is important for controlling inflammation and adverse immune responses, processes, and the diseases and disorders related thereto. Thus, the identification and characterization of the proteins involved in IKK-mediated cellular processes would benefit the art and be advantageous for providing therapies for those suffering from such disorders and diseases.

SUMMARY OF THE INVENTION

The present invention relates to methods of preventing and treating inflammatory and immune-related diseases or disorders using IκB kinase (IKK) inhibitors, compounds of formula (I) as described herein. Also provided is the IKK inhibitor 4(2'-aminoethyl)amino-1,8-dimethylimidazo(1,2-a)quinoxaline used to prevent and treat inflammatory and immune-related diseases or disorders.

It is an object of the present invention to provide methods of preventing and treating inflammatory and immune-related diseases or disorders using IKK inhibitors either alone, or optionally, in combination with at least one biologically active agent.

It is also an object of the present invention to provide IKK inhibitors for the prevention and treatment of inflammatory and immune-related diseases or disorders.

It is another object of the present invention to provide pharmaceutical compositions comprising IKK inhibitors in a pharmaceutically-acceptable carrier, excipient, or diluent for use in preventing and treating inflammatory and immune-related diseases or disorders.

It is a further object of the present invention to provide methods of preventing and treating diseases and disorders involving inflammation and the immune system. Preferably, the methods comprise the use of IKK inhibitors for the prevention and treatment of inflammatory and immune-related diseases, non-limiting examples of which include, rheumatoid arthritis, transplant rejection, inflammatory bowel disease, osteoarthritis, asthma, chronic obstructive pulmonary disease, atherosclerosis, psoriasis, multiple sclerosis, stroke, systemic lupus erythematosus, Alzheimer's disease, brain ischemia, traumatic brain injury, Parkinson's disease, amyotrophic lateral sclerosis, subarachnoid hemorrhage or other diseases or disorders associated with excessive production of inflammatory mediators in the brain and central nervous system.

Yet another object of the present invention is to provide methods of inhibiting i) the catalytic activity of IKK; ii) the phosphorylation of IκB; and/or iii) NF-κB gene expression using IKK inhibitors for the prevention and treatment of inflammatory and immune-related diseases or disorders.

A more particular object of the present invention is to provide an IKK inhibitor, 4(2'-aminoethyl)amino-1,8-dimethylimidazo(1,2-a) quinoxaline, also known as compound 6 herein, or a pharmaceutically-acceptable salt thereof, useful as a preventative and/or therapeutic agent and in methods of treating inflammatory and immune diseases. In accordance with the present invention, compound 6 is shown by the below formula,

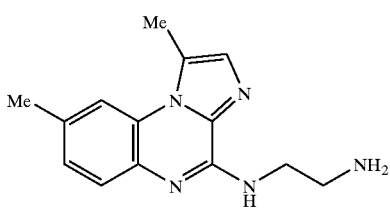

6

Yet another embodiment of the present invention relates to 4-amino substituted benzoquinoline, benzoquinoxaline, and benzoquinazoline compounds having five-membered heterocycles (e.g., pyrazolyl, imidazolyl, and thiazolyl rings) fused thereto. The compounds are useful as anti-inflammatory agents and/or for treating conditions associated with TNF-α and NF-κB activity.

It is a further object of the present invention to provide 4-amino substituted benzoquinoline, benzoquinoxaline, and benzoquinazoline compounds having five-membered heterocycles (e.g., pyrazolyl, imidazolyl, and thiazolyl rings) fused thereto, more specifically, the compounds of formula (I), as described herein. The compounds are useful as anti-inflammatory agents and/or for preventing and treating conditions associated with TNF-α and NF-κB.

One embodiment of the present invention is further directed to a compound of the formula (I), useful in treating inflammatory diseases or disorders:

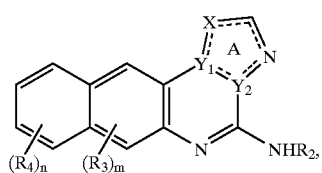

(I)

or a pharmaceutically-acceptable salt thereof, wherein

X is $NR_1$, $CR_1$, or S;

$Y_1$ and $Y_2$ are nitrogen or carbon, provided that
a) when X is $CR_1$, at least one of $Y_1$ and $Y_2$ is nitrogen; and
b) when one of $Y_1$ and $Y_2$ is carbon, the other of $Y_1$ and $Y_2$ is nitrogen and/or X is $NR_1$ or S, so that ring A defines a five-membered heteroaryl ring having at least two heteroatoms;

$R_1$ is hydrogen, halogen, alkyl, substituted alkyl, cyano, $OR_5$, $NR_5R_6$, $C(=O)R_5$, $CO_2R_5$, or aryl;

$R_2$ is alkyl, substituted alkyl, alkenyl, alkynyl, alkoxy, alkylthio, aryl, heteroaryl, heterocyclo, cycloalkyl, or substituted cycloalkyl;

$R_3$ and $R_4$ are independently selected from halogen, alkyl, substituted alkyl, nitro, cyano, $OR_7$, $NR_7R_8$, $C(=O)$ $R_7$, $CO_2R_7$, $C(=O)NR_7R_8$, $NR_7C(=O)R_8$, $NR_7C(=O)OR_8$, $S(O)_qR_7$, $NR_7SO_2R_8$, and $SO_2NR_7R_8$;

$R_5$, $R_6$, $R_7$, and $R_8$ are independently selected from hydrogen, alkyl, substituted alkyl, and phenyl, or when attached to the same nitrogen atom (as in $NR_5R_6$ or $NR_7R_8$) can join together to form a heterocycle or heteroaryl; and m, n and q are independently 0, 1, or 2.

Advantageously, $R_2$, as specified above, is an alkyl optionally substituted with OR' or NR'R", as defined in the specification. The invention also relates to pharmaceutical compositions containing at least one compound of formula (I) and a pharmaceutically-acceptable carrier or diluent. Also included within the invention are methods of preventing and treating inflammatory and immune-related diseases and disorders comprising administering to a mammal in need of such prevention and/or treatment an effective amount of at least one compound of formula (I).

Another object of the present invention is to provide kits for treating inflammatory and immune-related diseases and disorders, comprising one or more IKK inhibitors, compound 6, and/or compounds of formula (I) as described herein.

DESCRIPTION OF THE INVENTION

Figure 1:
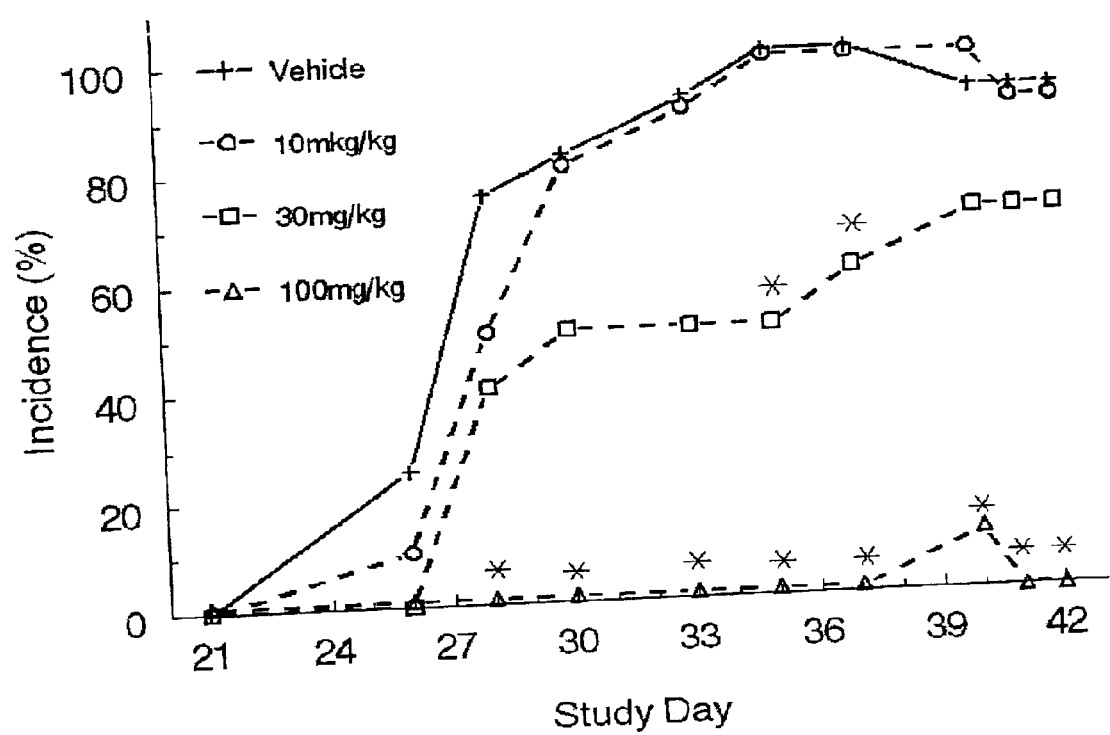
FIG. 1 shows the effect of 4(2'-aminoethyl)amino-1,8-dimethylimidazo(1,2-a)quinoxaline (compound 6) on disease incidence in the murine model of collagen-induced arthritis. The compound was administered once daily in a preventative dosing mode. *$p<0.05$, Fisher's Exact test.

The present invention describes methods of preventing and treating inflammatory and immune-related diseases or disorders using inhibitors of IκB kinase (IKK). Such methods are efficacious in vivo in inhibiting IKK activity in mammalian, including human and biological systems, e.g. animal models of disease.

In one of its aspects, the present invention relates to methods of inhibiting the catalytic activity of IKK using inhibitors. The inhibitors of the present invention preferably inhibit the catalytic activity of the IKKs (see, Example 2). For example, inhibitors can include small molecule enzyme inhibitors which bind directly to the enzyme, preferably IKK, and more preferably IKK-2. Without wishing to be bound by theory, it is believed that the binding of the inhibitor to the active site of IKK also inhibits binding of substrate, such as, for example, IκB or ATP.

One embodiment of the present invention provides a novel IKK inhibitor, 4(2'-aminoethyl)amino-1,8-dimethylimidazo(1,2-a)quinoxaline (compound 6), wherein the compounds of the present invention can be used in methods for the prevention and treatment of inflammatory and immune-related diseases or disorders.

Another embodiment of the present invention provides 4-amino substituted benzoquinoline, benzoquinoxaline, and benzoquinazoline compounds having five-membered heterocycles (e.g., pyrazolyl, imidazolyl, and thiazolyl rings) fused thereto. The compounds are useful as anti-inflammatory agents and/or for treating conditions associated with TNF-α and NF-κB.

Also provided are pharmaceutical compositions comprising IKK inhibitor compounds or salts thereof, and kits comprising IKK inhibitor compounds or salts thereof.

Definitions

The following definitions are provided to more fully describe the present invention in its various aspects. The definitions are intended to be useful for guidance and elucidation, and are not intended to limit the disclosed invention and its embodiments.

The term "IκB" as used herein, is defined as Inhibitor κB. The IκB family comprises IκBα, IKBβ, and IκBε, all of which contain ankyrin repeats for complexing to NF-κB.

The term "IKK" as used herein, refers to IκB-kinase (IKK). IKK comprises two catalytic subunits, IKK-1 and IKK-2, also known as IKKα and IKKβ, respectively.

"Activation of IKK" as used herein means changing an inactive IKK protein into an active IKK protein that functions as an IκB kinase. Activated IKK phosphorylates serine-32 and serine-36 of IκB, which thus marks the IκB for ubiquitination and degradation.

"IKK inhibitors" according to the invention refer to those compounds or molecules which prevent, block, abolish, antagonize, suppress, or reduce the activation of IKK as defined above. In addition, IKK inhibitors inhibit the activity of IKK, preferably the in vivo activity of IKK, such that one or more of the following occurs: 1) inhibition of IKK catalytic activity; 2) inhibition of IκB phosphorylation, preferably catalyzed phosphorylation of IκB; and/or 3) inhibition of NF-κB-dependent gene expression activation.

A "selective inhibitor", as referred to herein, inhibits one protein at a higher level or degree than another protein. An inhibitor is considered to be selective for one protein over another protein when there is preferably at least about a 5-fold or greater difference in inhibition of one protein compared with another protein. More preferably, there is at least about an 8-fold or greater difference in inhibition of one protein compared with another protein.

"Nuclear factor-κB" or "N F-κB" as used herein, is defined as a ubiquitously expressed family of eukaryotic transcription factors. This family comprises a homo- or hetero-dimer of DNA-binding proteins related to c-Rel, a proto-oncogene that controls the expression of many κB-dependent immune, inflammatory, and anti-apoptotic response genes.

The phrase "NF-κB-dependent gene expression" as used herein, is defined as those immune-related and inflammatory genes that are under the regulatory control of the κB-enhancer. In most cells, NF-κB exists in a dormant state in the cytoplasm bound to inhibitory proteins, collectively called IκB, that conceal the nuclear localization signal, thereby preventing nuclear translocation. Activation of NF-κB can be induced by cytokines, such as TNFα and IL-1, where both TNF-α and IL-1 signaling results in sequential phosphorylation and activation of a cascade of proteins. Specifically, activation of IKK or modification of the catalytic action of IKK results in phosphorylation, ubiquitination, and degradation of IκB.

The term "treat", "treating", or "treatment" refers to the prevention, reduction, or amelioration, partial or complete alleviation, or cure of a disease, disorder, or condition. NF-κB plays an important role in inflammation and immune response; therefore, the inhibition of IκB phosphorylation can also be an important target for novel anti-inflammatory and immune-related agents.

The phrase "NF-κB-associated condition" refers to diseases that are characterized by release of NF-κB from the cytoplasm (e.g., upon phosphorylation of IκB).

The phrase "TNF-α-associated condition" is a condition characterized by enhanced levels of TNF-α. In the instant specification, the term NF-κB-associated condition includes a TNF-α-associated condition but is not limited thereto as NF-κB is involved in the activity and upregulation of other pro-inflammatory proteins and genes.

The term "inflammatory or immune diseases or disorders" is used herein to encompass both IKK-associated conditions, NF-κB-associated conditions, TNF-α-associated conditions, e.g., any condition, disease, or disorder that is associated with release of NF-κB and/or enhanced levels of TNF-α, including each of the conditions specifically referenced below.

"Bioavailability" as referred to herein is the rate and extent to which an active ingredient or moiety is absorbed from a pharmaceutical composition and becomes available at the site of action. For drug products that are not intended to be absorbed into the bloodstream, bioavailability may be assessed by measurements intended to reflect the rate and extent to which the active ingredient or active moiety becomes available at the site of action.

The term "prodrug" denotes a therapeutic agent that is prepared in an inactive form, which upon administration to a subject, undergoes chemical conversion by metabolic or chemical processes by the action of endogenous enzymes or other chemicals and/or conditions, to yield the active compounds of the present invention, and/or salt and/or solvate thereof. For example, compounds containing a carboxy group can form physiologically hydrolyzable esters which serve as prodrugs by being hydrolyzed in the body to yield formula I-II compounds per se.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When numbers appear in subscript after the symbol "C", the subscript defines with more specificity the number of carbon atoms that a particular group can contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth.

The term "substituted alkyl" refers to an alkyl group as defined above having one, two, or three substituents selected from the group consisting of halo, amino, cyano, hydroxy, alkoxy, alkylthio, —C(=O)H, —CO$_2$H, —(C=O)alkyl, —CO$_2$alkyl, cycloalkyl, substituted cycloalkyl, aryl, heteroaryl, or heterocycle. Thus, the term "substituted alkyl" includes a polyfluoroalkyl, i.e., where two or more hydrogen atoms of an alkyl chain are replaced by a fluorine atom, such as with trifluoromethyl. The term "substituted alkyl" also includes an alkyl group as defined above having the substituent NR'R", wherein each of R' and R" are independently selected from the group consisting of hydrogen, alkyl, substituted alkyl, hydroxy, alkoxy, —C(=O)H, —CO$_2$H— (C=O)alkyl, —CO$_2$-alkyl, cycloalkyl, substituted cycloalkyl, aryl, heteroaryl, and heterocycle. Alternatively, R' and R" can together form a heterocyclo or heteroaryl ring.

A substituted lower alkyl or substituted $C_{1-4}$alkyl refers to an alkyl group of 1–4 carbon atoms having one to three substituents selected from those recited above for alkyl groups generally.

The term "alkoxy" refers to an alkyl group as defined above bonded through an oxygen atom (—O—), and the term "alkylthio" refers to an alkyl group as defined above bonded through a sulfur atom (—S—). For example, such groups include methoxy, methylthio, ethoxy, ethylthio, n-propoxy, n-propylthio, isopropoxy, isopropylthio, n-butoxy, n-butylthio, tert-butoxy, tert-butylthio, n-pentoxy, n-pentylthio, and so forth.

The term "alkenyl" refers to straight or branched chain hydrocarbon groups having 2 to 12 carbon atoms and at least one double bond. Alkenyl groups having 2 to 6 carbon atoms and one double bond are most preferred. Exemplary alkenyl groups include ethenyl, 1-methyl-ethenyl, 1- or 2-propenyl, 1-methyl-1-propenyl, 1-methyl-2-propenyl, 1,1-dimethyl-2-propenyl, 2-methyl-2-propenyl, 1-, 2- or 3-butenyl, 1-methyl-1-butenyl, 2-methyl-1-butenyl, 3-methyl-1-butenyl, 3,3-dimethyl-1-butenyl, 2,3-dimethyl-1-butenyl, 1-methyl-2-butenyl, 1,1-dimethyl-2-butenyl, 2-methyl-2-butenyl, 3-methyl-2-butenyl, 1,3-butadienyl, 1,3-dimethyl-1,3-butadienyl, 1-, 2-, 3- or 4-pentenyl, and so forth.

The term "alkynyl" refers to straight or branched chain hydrocarbon groups having 2 to 12 carbon atoms and at least one triple bond. Alkynyl groups of 2 to 6 carbon atoms and having one triple bond are most preferred. Exemplary alkynyl groups include ethynyl, 1- or 2-propynyl, 1-methyl-2-propynyl, 1,1-dimethyl-2-propynyl, 1-, 2- or 3-butynyl, 3-methyl-1-butynyl, 3,3-dimethyl-1-butynyl, 1-methyl-2-butynyl, 1,1-dimethyl-2-butynyl, 1-, 2- 3-, or 4-pentynyl, and so forth.

The term "amino" when used alone refers to NH2. When used to define a substituent, as in 4-amino substituted tetracycles, the term "amino" refers to the group NR'R", wherein R' and R" are as defined above for alkyl.

The term "carbonyl" refers to —C(=O)—, and "carboxy" refers to —CO$_2$—. Thus, carbonylC1–4alkyl refers to the group —C(=O) linked to a $C_{1-4}$ alkyl.

The term "halo" or "halogen" refers to chloro, bromo, fluoro and iodo.

The term "cycloalkyl" refers to fully saturated and partially unsaturated hydrocarbon rings of 3 to 9, preferably 3 to 7, carbon atoms as well as such rings having a fused aryl ring such as indan or a bridge of three to four carbon atoms as in bicycloheptane.

The term "substituted cycloalkyl" refers to such rings having one, two, or three substituents, preferably one, selected from the group consisting of alkyl, substituted alkyl, alkoxy, alkylthio, halo, hydroxy, cyano, amino, —NH(alkyl), —NH(cycloalkyl), —N(alkyl)$_2$, —CO$_2$H, —CO$_2$lower alkyl, aryl, heterocyclo, heteroaryl, keto (=O), =N—OH, =N—O-lower alkyl, and a five or six membered ketal, i.e., 1,3-dioxolane or 1,3-dioxane.

The term "aryl" refers to phenyl, 1-naphthyl and 2-naphthyl, with phenyl being preferred. When the term "aryl" is used, it encompasses such rings having from zero, one, two or three substituents selected from the group consisting of alkyl, substituted alkyl, alkoxy, alkylthio, halo, hydroxy, nitro, cyano, amino, —NH(alkyl), —NH(cycloalkyl), —N(alkyl)$_2$, —CO$_2$H, —(C=O)alkyl, —CO$_2$-alkyl, cycloalkyl, substituted cycloalkyl, —(C=O)NH$_2$, —(C=O)NH(alkyl), —(C=O)NH(cycloalkyl), —(C=O)N(alkyl)$_2$, —NH—CH$_2$—CO$_2$H, —NH—CH$_2$—CO$_2$-alkyl, phenyl, benzyl, phenylethyl, phenyloxy, phenylthio, heterocyclo, and heteroaryl.

The term "heterocyclo" or "heterocycle" refers to substituted and unsubstituted non-aromatic 3 to 7 membered monocyclic groups, 7 to 11 membered bicyclic groups, and 10 to 15 membered tricyclic groups which have at least one heteroatom (O, S, or N) in at least one of the rings. When the heterocyclo is monocyclic, five- or six-membered rings are preferred; when bicyclic, fused 5,6- or 6,6-membered ring systems are preferred; and when tricyclic, ring systems having one five and two six membered rings, or three six membered rings, are preferred. Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing the bicyclic and tricyclic groups can contain only carbon atoms and can be saturated, partially saturated, or unsaturated. The nitrogen and sulfur atoms can optionally be oxidized and the nitrogen atoms can optionally be quaternized. The heterocyclo group can be attached at any available nitrogen or carbon atom.

Whenever the term "heterocyclo" or "heterocycle" is used, any ring of the heterocyclo group can optionally contain one, two, or three substituents selected from the group consisting of halo, amino, cyano, alkyl, substituted alkyl, —NH(alkyl), —NH(cycloalkyl), —N(alkyl)$_2$, alkoxy, alkylthio, hydroxy, nitro, phenyl, benzyl, phenylethyl, phenyloxy, phenylthio, —CO$_2$H, —CO2-alkyl, cycloalkyl, substituted cycloalkyl, —(C=O)NH$_2$, —(C=O)NH(alkyl), —(C=O)NH(cycloalkyl), —(C=O)N(alkyl)$_2$, —NH—CH$_2$—CO$_2$H, —NH—CH$_2$—CO$_2$-alkyl, heterocyclo, heteroaryl, keto, =N—OH, =N—O-lower alkyl, and a five or six membered ketal, i.e., 1,3-dioxolane or 1,3-dioxane.

Exemplary monocyclic groups include tetrahydrothienyl, tetrahydrofuryl, azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. When the heteroaryl is monocyclic, five- or six membered rings are preferred; when bicyclic, fused 5,6- or 6,6-membered ring systems are preferred; and when tricyclic, ring systems having one five and two six membered rings, or three six-membered rings, are preferred. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups can contain only carbon atoms and can be saturated, partially saturated, or unsaturated. The nitrogen and sulfur atoms can optionally be oxidized and the nitrogen atoms can optionally be quaternized. Heteroaryl groups which are bicyclic or tricyclic include at least one fully aromatic ring but the other fused ring or rings can be aromatic or non-aromatic. The heteroaryl group can be attached at any available nitrogen or carbon atom of any ring.

Whenever the term "heteroaryl" is used herein, any ring of the heteroaryl group can optionally contain one, two or three substituents selected from the group consisting of halo, amino, cyano, alkyl, substituted alkyl, —NH(alkyl), —NH (cycloalkyl), —N(alkyl)$_2$, alkoxy, alkylthio, hydroxy, nitro, phenyl, benzyl, phenylethyl, phenyloxy, phenylthio, —CO$_2$H, —CO$_2$-alkyl, cycloalkyl, substituted cycloalkyl, —(C=O)NH$_2$, —(C=O)NH(alkyl), —(C=O)NH (cycloalkyl), —(C=O)N(alkyl)$_2$, —NH—CH$_2$—CO$_2$H, —NH—CH$_2$—CO$_2$-alkyl, heterocyclo, and heteroaryl.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, triazolyl, and the like.

Exemplary bicyclic heteroaryl groups include indolyl, isoindolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, isobenzofuranyl, chromonyl, coumarinyl, benzopyranyl, cinnolinyl, quinoxalinyl, quinazolinyl, indazolyl, pyrrolopyridyl, furopyridinyl, dihydroisoindolyl, tetrahydroquinolinyl, napthyridinyl, pteridinyl, and the like.

Exemplary tricyclic heteroaryl groups include carbazolyl, benzidolyl, phenanthrollinyl, acridinyl, phenanthridinyl, xanthenyl and the like.

DETAILED DESCRIPTION OF THE INVENTION

Since activation of NF-κB-dependent gene expression is associated with the activation of IKK-dependent phosphorylation of IκB and genes involved in inflammatory and immune-related diseases or disorders, one emobidment of the present invention generally relates to the prevention and treatment of inflammatory and immune-related diseases, disorders, or conditions using IKK inhibitors. More specifically, embodiments of the present invention relate to: 1) methods of inhibiting IKK to prevent and/or treat inflammatory and immune-related diseases, disorders, or conditions; 2) methods of inhibiting the activation of NF-κB-dependent gene expression by inhibiting the IKK-dependent phosphorylation of IκB for preventing and treating inflammatory and/or immune-related diseases, disorders, or conditions; 3) inhibitors of IKK; 4) the use of inhibitors of IKK in the methods of the present invention; and 5) exemplary IKK inhibitor compounds which inhibit IKK.

As described herein, an embodiment of the present invention demonstrates the in vivo employment of an IKK inhibitor for use in methods for treating and preventing inflammatory and immune-related diseases or disorders (Examples 4–7). Prior to the present invention, there have been no demonstrations of the actual in vivo therapeutic effectiveness of IKK inhibitors in treating and preventing inflammatory or immune-related diseases, such as, for example, asthma, inflammatory bowel disease, tissue/organ transplant rejection, e.g., graft versus host rejection, and pulmonary diseases, for example, involving inflammatory cell infiltration in the lung.

Accordingly, an aspect of the present invention provides therapeutic and prophylactic methods of treating and preventing inflammatory or immune-related diseases, disorders, or conditions by administering an effective amount of one or more IKK inhibitors, or salt thereof, alone, or optionally, in combination with another IKK inhibitor, to a subject, preferably a mammal, in need thereof. In addition, other therapeutic or biologically active agents can be used in combination with the IKK inhibitors, for example, drugs, hormones, or synthetic agents, such as those described below, for example. In the methods of the present invention, such therapeutic or biologically active agents can be administered prior to, simultaneously with, or following the administration of one or more of the IKK inhibitors of the present invention.

More specifically, IKK inhibitors can also be used in accordance with the described methods in conjunction with other drugs, such as cyclosporine A or CTLA4-Ig, to alleviate transplant rejection. Cyclosporine A is a potent immunosuppressive compound currently used therapeutically in humans to prevent graft rejection following solid organ transplantation. Most current therapeutic protocols for transplant include cyclosporine A in combination with other potent immunosuppressive drugs such as steroids and antiproliferative agents such as mycophenolic acid. When test compounds are examined for clinical efficacy in solid organ transplant, the protocols generally include treatment of the patients with test compounds in addition to standard therapeutics including cyclosporine A. Therefore, in order to progress with clinical development of new compounds, new compounds must work beneficially well with cyclosporine A.

CTLA4-Ig is an immunoglobulin fusion protein that binds to the ligands for CD28 and CTLA4 (Linsley et al. J. Exp. Med., 174:561–569, 1991). CTLA4-Ig is a promising agent that is effective in the treatment of transplant rejection (Larsen et al., Nature, 381:434–438, 1996). Since some form of CTLA4-Ig could become part of the standard treatment paradigm for transplantation, new compounds developed for the prevention of graft rejection would be important, particularly in conjunction with CTLA4-Ig.

Embodiments of the present invention further embrace methods of inhibiting the IKK enzyme, comprising administering to an individual suffering from an inflammatory or immune-related disease or disorder, an IKK inhibitor in an amount effective to inhibit the catalytic activity of IKK and the IKK-dependent phosphorylation of IκB. Without wishing to be bound by theory, the mechanism of inhibition of IKK involves inhibiting the catalytic activity of the IKKs, either IKK-1 or IKK-2, preferably IKK-2, through binding to the active site of the enzyme and inhibiting the binding and/or phosphorylation of substrates such as IκB and ATP (see Example 2).

One embodiment of the present invention encompasses a method of inhibiting the phosphorylation of IκB inhibitor protein which comprises the administration of IKK inhibitors in an amount effective to inhibit the phosphorylation of the IκB protein. In particular, inhibition of IκB-α phosphorylation is preferred, and the inhibition of phosphorylation of IκB-α at serine-32 and serine-36 is more preferred.

According to the present invention, compounds which inhibit IKK, i.e. IKK inhibitors, can be used in the methods for preventing and treating inflammatory and immune system-related conditions, diseases, or disorders. Non-limiting examples of such diseases, disorders, and conditions include arthritis, rheumatoid arthritis, psoriatic arthritis, osteoarthritis, acute pancreatitis, chronic pancreatitis, psoriasis, glomerulonephritis, serum sickness, lupus (systematic lupus erythematosis), urticaria, scieraclerma, contact dermatitis, dermatomyositis, alopecia, atopic eczemas, ichthyosisrhinitis, inflammatory bowel disease (Crohn's and ulcerative colitis); Alzheimer's disease, brain ischemia, traumatic brain injury, Parkinson's Disease, Creutzfeldt-Jacob diseases, HIV encephalitis, cerebral malaria, and meningitis, atherosclerosis, ataxia telangiectasis, septic shock, multiple sclerosis, amyotrophic lateral sclerosis, atherosclerosis, subarachnoid hemorrhage, autoimmune diseases, systemic lupus erythematosus, multiple sclerosis, hematopoiesis, pulmonary diseases, respiratory allergies, asthma, acute respiratory distress syndrome, hayfever, allergic rhinitis, allergic respiratory disease, herpes simplex type 1 (HSV-1), herpes simplex type 2 (HSV-2), cytomegalovirus, Epstein-Barr, human immunodeficiency virus (HIV), Addison's disease (autoimmune disease of the adrenal glands), idiopathic adrenal insufficiency, autoimmune polyglandular disease (also known as autoimmune polyglandular syndrome), fungal infections, mycosis fungoides, chronic obstructive pulmonary disorder; tissue/organ transplant rejection (e.g., kidney, liver, heart, lung, pancreas, bone marrow, cornea, small bowel, skin allografts, skin homografts, and heterografts, etc.); stroke, oncological diseases, cancer, tumors, breast cancer, prostate cancer, and Hodgkin's lymphoma.

IKK inhibitors of the present invention can be used to prevent, treat or ameliorate diseases and conditions, particularly inflammatory or immune-related diseases or conditions. Without wishing to be bound by theory, the IKK inhibitors are employed in preventing and treating diseases, disorders, or conditions characterized by NF-κB activation via phosphorylation of IκB by IKK. Specifically, the embodiments of the present invention further relate to IKK inhibitors that inhibit the catalytic activity of the IKK enzyme, thereby blocking phosphorylation of IκB and downstream transcriptional activation of κB gene expression, such as NF-κB.

In one embodiment of the present invention, an IKK inhibitor has an $IC_{50}$ against IKK activity ranging from about 0.01 $\mu$M to about 50 $\mu$M. Preferably, the IKK inhibitor has an $IC_{50}$ against IKK activity ranging from about 0.01 $\mu$M to about 10 $\mu$M, more preferably from about 0.01 $\mu$M to about 5 $\mu$M, and most preferably from about 0.01 $\mu$M to about 1 $\mu$M.

Yet another embodiment of the present invention encompasses IKK inhibitors that have selectivity for IKK-2 over IKK-1 (see Example 2). Preferably, a selective IKK inhibitor has at least about a 5-fold or greater selectivity for IKK-2 over IKK-1. More preferably, a selective IKK inhibitor has at least about an 8-fold or greater selectivity for IKK-2 over IKK-1. As a more particular guide, for example, inhibition of IKK-2 activity is about 5- to 500-fold, or about 8- to 100-fold, relative to IKK-1 activity, preferably about 10- to 100-fold, and more preferably, about 10 to 50-fold.

In a preferred aspect, according to the invention, selective inhibitors affect about 50% inhibition of IKK activity at an $IC_{50}$ against IKK activity ranging from about 0.01 $\mu$M to about 50 $\mu$M. Preferably, selective inhibitors have an $IC_{50}$, against IKK activity ranging from about 0.01 $\mu$M to about 10 $\mu$M, and preferably, from about 0.01 $\mu$M to about 5 $\mu$M. Most preferably, selective inhibitors have an $IC_{50}$ ranging from about 0.01 $\mu$M to about 1 $\mu$M.

A preferred embodiment of the present invention comprises IKK inhibitors selective for IKK-2. Preferably, the selective IKK-2 inhibitor has an $IC_{50}$ against IKK-2 activity, ranging from about 0.01 $\mu$M to about 5 $\mu$M, and more preferably, an $IC_{50}$ against IKK-2 activity, ranging from about 0.01 $\mu$M to about 1 $\mu$M.

In another aspect, bioavailability of the inhibitor compounds was assessed. For example, the pharmacokinetics of compound 6 in mice is described in Example 3. For guidance, an effective oral bioavailability for the IKK inhibitor of the present invention ranges from about 10% to about 100%, preferably from about 50% to about 100%, and more preferably from about 80% to about 100%. From a pharmacokinetic perspective, bioavailability data for a given compound estimate the relative fraction of the orally administered dose that is absorbed into the systemic circulation when compared to the bioavailability data for a solution, suspension, or intravenous dosage form.

The present invention further relates to methods of testing the inhibitory potential of candidate IKK inhibitors. Specifically, Example 2 analyzes test compounds and their capacity to inhibit IKK activity by measuring the concentration of phosphorylated substrate, specifically IκB, and the concentration of test IKK inhibitor compound necessary to achieve 50% inhibition of IKK activity.

One embodiment of the present invention provides beneficial and advantageous in vivo animal studies using IKK inhibitors that demonstrate compound efficacy using methods of the present invention. For example, 4 (2'-aminoethyl) amino-1,8-dimethylimidazo(1,2-a) quinoxaline, compound 6 herein, or a salt thereof, newly discovered by the present inventors, inhibits the catalytic activity of IκB kinase by blocking the active site of IKK which is responsible for phosphorylating the IκB protein. Moreover, the examples described herein demonstrate that IKK inhibitors are particularly useful in methods of treating inflammatory and immune-related diseases or disorders in several different animal models of disease that are considered to be predictive of similar employment and effects in human patients.

The compounds and compositions of this invention are also useful in treating conditions that are characterized by release of NF-κB and/or enhanced levels of TNF-α. Inhibition or suppression of NF-κB and/or TNF-α may occur locally, for example, within certain tissues of the subject, or more extensively throughout the subject being treated for such a disease. Inhibition or suppression of NF-κB and/or TNF-α may occur by one or more mechanisms, e.g., by inhibiting or suppressing any step of the pathway(s), preferably inhibition of IKK. The present invention thus provides methods for treating such conditions, comprising administering to a subject in need thereof an effective amount of at least one compound of formula (I), compound 6, or salt thereof. Other therapeutic agents such as those described below may be employed in combination with the IKK inhibitors, compound 6, and/or compounds of formula (I). In the methods of the present invention, such other therapeutic agent(s) may be administered prior to, simultaneously with, or following the administration of the inventive compound.

Compound 6 is structurally represented by the following formula as shown below:

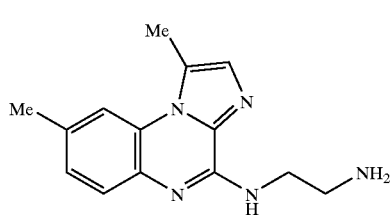

6

The formula of compound 6 or 4(2'-aminoethyl)amino-1,8-dimethylimidazo(1,2-a)quinoxaline forms salts which are also within the scope of the present invention. Unless otherwise indicated, reference to an IKK compound according to this invention is understood to include reference to salts thereof, as further described below.

In another embodiment of the present invention compounds of formula (I) are useful in treating inflammatory diseases or disorders:

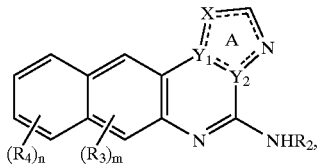

(I)

or a pharmaceutically-acceptable salt thereof, wherein

X is $NR_1$, $CR_1$, or S;

$Y_1$ and $Y_2$ are nitrogen or carbon, provided that a) when X is $CR_1$, at least one of $Y_1$ and $Y_2$ is nitrogen; and b) when one of $Y_1$ and $Y_2$ is carbon, the other of $Y_1$ and $Y_2$ is nitrogen and/or X is $NR_1$ or S, so that ring A defines a five-membered heteroaryl ring having at least two heteroatoms;

$R_1$ is hydrogen, halogen, alkyl, substituted alkyl, cyano, $OR_5$, $NR_5R_6$, $C(=O)R_5$, $CO_2R_5$, or aryl;

$R_2$ is alkyl, substituted alkyl, alkenyl, alkynyl, alkoxy, alkylthio, aryl, heteroaryl, heterocyclo, cycloalkyl, or substituted cycloalkyl;

$R_3$ and $R_4$ are independently selected from halogen, alkyl, substituted alkyl, nitro, cyano, $OR_7$, $NR_7R_8$, $C(=O)R_7$, $CO_2R_7$, $C(=O)NR_7R_8$, $NR_7C(=O)R_8$, $NR_7C(=O)OR_8$, $S(O)_qR_7$, $NR_7SO_2R_8$, and $SO_2NR_7R_8$;

$R_5$, $R_6$, $R_7$, and $R_8$ are independently selected from hydrogen, alkyl, substituted alkyl, and phenyl, or when attached to the same nitrogen atom (as in $NR_5R_6$ or $NR_7R_8$) can join together to form a heterocycle or heteroaryl; and m, n and q are independently 0, 1, or 2.

Yet another embodiment of the present invention encompasses the compounds having the formula (If):

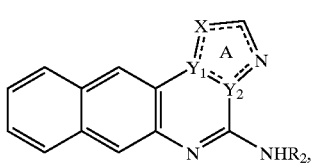

(If)

and pharmaceutically-acceptable salts thereof, wherein

X is $NR_1$, $CR_1$, or S;

$Y_1$ and $Y_2$ are nitrogen or carbon. provided that a) when X is $CR_1$, one of $Y_1$ and $Y_2$ is nitrogen, and b) when one of $Y_1$ and $Y_2$ is carbon, either the other of $Y_1$ and $Y_2$ is nitrogen or X is $NR_1$ or S, so that ring A defines a five-membered heteroaryl ring having two heteroatoms;

$R_1$ is hydrogen, halogen, lower alkyl, or substituted lower alkyl;

$R_2$ is alkyl or substituted alkyl,

More preferred are the compounds of formula (If), above, and/or pharmaceutically acceptable salts thereof, wherein X is $NR_1$ or $CR_1$;

$R_1$ is hydrogen, halogen, lower alkyl, or trifluoromethyl;

$R_2$ is $C_{1-2}$ alkyl optionally substituted with $OR_9$ or $NR_{10}R_{11}$;

$R_9$ is hydrogen or lower alkyl; and $R_{10}$ and $R_{11}$ are (i) independently selected from hydrogen, $C_{1-2}$alkyl, $C^{1-2}$substituted alkyl, and $-(C=O)C_{1-2}$ alkyl, or alternatively (ii) together form a five to six membered heterocycle or heteroaryl.

Most preferred are the compounds of formula (If), above, and/or pharmaceutically acceptable salts thereof, wherein ring A is selected from:

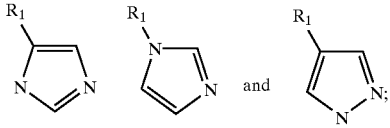

$R_1$ is hydrogen, halogen, ethyl, methyl, or trifluoromethyl; and $R_2$ is a $C_{1-2}$ alkyl optionally substituted with one of: OH, $NH_2$, $NH(C_{1-2}alkyl)$, $N(C_{1-2}alkyl)_2$, $NH(C_{1-2}$substituted alkyl), $N(C_{1-2}$substituted alkyl)$_2$, $NH(C=O)C_{1-2}$alkyl, and piperidinyl.

Advantageously, $R_1$ does not include hydroxy or an alkyl substituted with hydroxy.

When reference is made herein to a bond having a solid and dashed line, such as in [⫽], it should be understood that the bond(s) can be selected from a single or a double bond, as appropriate, given selections for adjacent atoms. For example, when there is shown

if X is sulfur or NH, the bonds linking X to adjacent atoms A and B are single bonds. However, when in

X is $CR_1$ or a nitrogen atom, one of the bonds linking X to A or B is a double bond and the other is a single bond.

Throughout this disclosure, groups and substituents thereof can be chosen by one skilled in the field to provide stable moieties and compounds.

The compounds of formula (I) and/or compound 6 form salts which are also within the scope of this invention. Unless otherwise indicated, reference to an inventive compound is understood to include reference to salts thereof. The term "salt(s)" denotes acidic and/or basic salts formed with inorganic and/or organic acids and bases. In addition, the term "salt(s) can include zwitterions (inner salts), e.g., when a compound of formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts can be useful, e.g., in isolation or purification steps which can be employed during preparation, and thus, are contemplated within the scope of the invention. Salts of the compounds of the formula (I) can be formed, for example, by reacting a compound of the formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as TEA, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups can be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Sodium or potassium salts are preferred.

Compounds of the formula (I) and/or compound 6 and salts thereof can exist in their tautomeric form, in which hydrogen atoms are transposed to other parts of the molecules and the chemical bonds between the atoms of the molecules are consequently rearranged. It should be understood that the all tautomeric forms, insofar as they can exist, are included within the invention. Additionally, inventive compounds can have trans and cis (E and Z) isomers and can contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended.

Another embodiment of the present invention relates to pharmaceutical or physiological compositions having at least one IKK inhibitor, or salt thereof, and preferably containing a pharmaceutically or physiologically acceptable vehicle, such as a carrier, diluent, or excipient. Furthermore, these pharmaceutical or physiological compositions comprise one or more IKK inhibitors, or salt thereof, either alone or in combination with a biologically active agent, such as but not limited to drugs, steroids, or synthetic compounds, particularly for use in the methods according to the present invention. The pharmaceutical compositions can preferably comprise any one of the IKK inhibitors of the present invention, for example, 4(2'-aminoethyl)amino-1,8-dimethylimidazo(1,2-a)quinoxaline (compound 6) or any one of the compounds of formula (I). Such a pharmaceutical or physiological composition can be administered to any individual in need of such therapy, including, for example, mammals such as monkeys, dogs, cats, cows, horses, rabbits, and most preferably, humans, for any of the above-described therapeutic or preventative uses and effects.

More particularly, the present invention also provides pharmaceutical compositions capable of treating conditions that are related to the activity of NF-κB, TNF-α, and/or enzymes modulating NF-κB and/or TNF-α levels such as IKK. Such compositions may contain other therapeutic agents and may be formulated, as described herein.

In the method embodiments of the present invention, IKK inhibitors, or pharmaceutical or physiological compositions thereof, can be administered alone or in combination with at least one other biologically active agent, which can be introduced in any sterile, biologically compatible pharmaceutical or physiologically acceptable carrier, excipient, or diluent, including, but not limited to, saline, buffered saline, dextrose, and water. The compositions can be administered to a patient alone, or optionally in combination with other biologically active agents, drugs, or hormones.

Additionally, in the methods according to this invention, the IKK inhibitors, or pharmaceutical or physiological compositions thereof, can be administered by any means suitable for the condition to be treated, which can depend on the need for site-specific treatment or quantity of drug to be delivered, by any number of routes including, but not limited to, oral, nasal, intravenous, intramuscular, intra-arterial, intramedullary, intrathecal, intraventricular, transdermal, subcutaneous, intraperitoneal, intranasal, enteral, topical, and sublingual means. Preferably, IKK inhibitors are administered orally, nasally, topically, or by inhalation.

Administration of IKK inhibitor compositions of the invention can also include local or systemic administration, including injection, oral administration, particle gun, or catheterized administration, and topical administration. Various methods can be used to administer an IKK inhibitor composition directly to a specific site in the body. For example, in instances where topical delivery is preferred, generally for skin-related diseases, transdermal patches and/or permeation enhancers can be used, a variety of which are commonly known in the art. Systematic treatment is preferred for cancerous or pre-cancerous conditions, although other modes of delivery are contemplated.

Both the dose of an IKK inhibitor, or composition thereof, and the means of administration can be determined based on the specific qualities of the IKK inhibitor or therapeutic composition thereof; the condition, age, and weight of the patient; the progression of the disease; and other relevant factors. Preferably, an IKK inhibitor, or therapeutic composition thereof, according to the invention, increases or decreases gene expression of NF-κB. Methods well known in the art can be used to determine the effectiveness of the mechanism chosen to alter expression of the NF-κB gene, such as hybridization of nucleotide probes to mRNA of the NF-κB gene, quantitative RT-PCR, or detection of an NF-κB protein using specific antibodies (e.g. Santa Cruz Biotechnology; Santa Cruz, Calif.).

In addition to the active ingredients, the pharmaceutical compositions can contain suitable pharmaceutically acceptable carriers, diluents, or excipients comprising auxiliaries which facilitate processing of the active compounds into preparations which can be used pharmaceutically. Further details on techniques for formulation and administration are provided in the latest edition of Remington's Pharmaceutical Sciences (Mack Publishing Co.; Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

The compounds of the present invention can be delivered orally, such as in the form of tablets, capsules, granules, powders, or liquid formulations including syrups; topically, such as in the form of solutions, suspensions, gels, creams, or ointments; nasally such as by inhalation spray; parenterally, such as by subcutaneous, intravenous, intramuscular or intrasternal injection or infusion techniques (e.g., as sterile injectable aqueous or non-aqueous solutions or suspensions); rectally such as in the form of suppositories; sublingually; bucally; or liposomally.

Pharmaceutical preparations for oral use can be obtained by the combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums, including arabic and tragacanth, and proteins such as gelatin and collagen. If desired, disintegrating or solubilizing agents can be added, such as cross-linked polyinyl pyrrolidone, agar, alginic acid, or a physiologically acceptable salt thereof, such as sodium alginate.

Pharmaceutical preparations, which can be orally administered in the methods according to the present invention, include push-fit capsules made of gelatin, as well as soft, scaled capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The inventive compounds can also be orally delivered by sublingual and/or buccal administration, e.g., with molded, compressed, or freeze-dried tablets. Exemplary compositions can include fast-dissolving diluents such as mannitol, lactose, sucrose, and/or cyclodextrins. Also included in such formulations are high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers can also be added for ease of fabrication and use.

Exemplary compositions for rectal administration include suppositories which can contain, for example, suitable non-irritating excipients, such as cocoa butter, synthetic glyceride esters or polyethylene glycols, which are solid at ordinary temperatures but liquefy and/or dissolve in the rectal cavity to release the drug.

Dragee cores can be used in conjunction with physiologically suitable coatings, such as concentrated sugar solutions, which can also contain gum arabic, talc, polyinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification, or to characterize the quantity of active compound, i.e., dosage.

Pharmaceutical formulations suitable for parenteral administration in the methods of the present invention can be formulated in aqueous solutions, preferably in physiologically compatible buffers such as Hanks' solution, Ringer's solution, or physiologically buffered saline. Aqueous injection suspensions can contain substances which increase the viscosity of the suspension, such as sodium carboxymethyl cellulose, sorbitol, or dextran. In addition, suspensions of the active compounds can be prepared as appropriate oily injection suspensions. Suitable lipophilic solvents or vehicles include fatty oils such as sesame oil, or synthetic fatty acid esters, such as ethyloleate or triglycerides, or liposomes. Optionally, the suspension can also contain suitable stabilizers or agents which increase the solubility of the compounds to allow for the preparation of highly concentrated solutions. Additional exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

For topical or nasal administration, penetrants or permeation-enhancing agents that are appropriate to the particular barrier to be permeated are used in the formulation. Such penetrants are generally known in the art. Exemplary compositions for topical administration include a topical carrier such as PLASTIBASE® (mineral oil gelled with polyethylene). Exemplary compositions for nasal aerosol or inhalation administration include solutions which can contain, for example, benzyl alcohol or other suitable preservatives, absorption promoters to enhance absorption and/or bioavailability, and/or other solubilizing or dispersing agents such as those known in the art.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes.

Dosage unit formulations containing non-toxic, pharmaceutically acceptable vehicles or diluents can be administered. The compounds can be administered in a form suitable for immediate release or extended release. Immediate release or extended release can be achieved with suitable pharmaceutical compositions or, particularly in the case of extended release, with devices such as subcutaneous implants or osmotic pumps.

The IKK inhibitor, or pharmaceutical composition thereof, can be provided as a salt and can be formed with many acids, including but not limited to, hydrochloric, sulfuric, acetic, lactic, tartaric, malic, succinic, and the like. Salts tend to be more soluble in aqueous solvents, or other protonic solvents, than are the corresponding free base forms. In other cases, the preferred preparation can be a lyophilized powder which can contain any or all of the following: 1–50 mM histidine, 0.1%–2% sucrose, and 2–7% mannitol, at a pH range of 4.5 to 5.5, combined with a buffer prior to use. After the pharmaceutical compositions have been prepared, they can be placed in an appropriate container and labeled for treatment of an indicated condition. For administration of IKK inhibitors, such labeling would include amount, frequency, and method of administration.

Pharmaceutical compositions comprising one or more IKK inhibitors suitable for use in the present invention include compositions in which the active ingredients are contained in an amount effective to achieve the intended purpose. The determination of an effective dose or amount is well within the capability of those skilled in the art. For any compound, the therapeutically effective dose can be estimated initially either in cell culture assays, e.g., using neoplastic cells, or in animal models, usually mice, rats, rabbits, dogs, or pigs. The animal model can also be used to determine the appropriate dosage, concentration range and route of administration. Such information can then be used and extrapolated to determine useful doses, concentration ranges, and routes for administration in humans. For guidance, in accordance with the methods of the present invention, an effective amount of IKK inhibitor optimally results in a level of inhibition of IKK activity ranging from about 20–100%, preferably, about 50–100%, more preferably about 80–100%, and most preferably about 90–100%, for the treatment of inflammatory and/or immune-related diseases.

A therapeutically effective dose refers to that amount of active ingredient or compound, such as an IKK inhibitor, which ameliorates, reduces, or eliminates the symptoms, condition, disease, or disorder. Therapeutic efficacy and toxicity can be determined by standard pharmaceutical procedures in cell cultures or experimental animals, e.g., ED50 (the dose therapeutically effective in 50% of the population) and LD50 (the dose lethal to 50% of the population). The dose ratio of therapeutic to toxic effects is the therapeutic index, which can be expressed as the ratio, ED50/LD50. Pharmaceutical compositions which exhibit large therapeutic indices are preferred. As understood by the skilled practitioner, data obtained from cell culture assays and animal studies are used in determining a range of dosages for human use. Preferred dosage of a pharmaceutical composition is within a range of circulating concentrations that include the $ED_{50}$ with little or no toxicity. The dosage varies within this range depending upon the dosage form employed, sensitivity of the patient, and the route of administration.

It will be understood that the specific dose level and frequency of dosage for any particular subject can be varied and will depend upon a variety of factors; the exact dosage will be determined by the practitioner, who will consider the factors related to the individual requiring treatment. Dosage and administration are adjusted to provide sufficient levels of the IKK inhibitor active moiety or to maintain the desired effect. Factors which are taken into account include the severity of the individual's disease state, general health of the patient, age, weight, and gender of the patient, diet, and mode, time and frequency of administration, rate of excretion, drug combination(s), reaction sensitivities, and tolerance/response to therapy. As a general guide, long-acting pharmaceutical compositions can be administered every 3 to 4 days, every week, or once every two weeks, depending on half-life and clearance rate of the particular formulation.

Normal dosage amounts can vary from about 0.1 to about 100,000 micrograms (μg), up to a total dose of about 1 gram (g), depending upon the route of administration. Preferably, dosages range from about 1 to about 100 μg. Guidance as to particular dosages and methods of delivery is provided in the literature, via empirical determination, and is generally available to, and routinely able to be determined by practitioners in the art. Single or multiple doses can be administered on, for example, a daily, every other day, or weekly schedule. In particular, the effective amount of a compound of the present invention can be determined by one of ordinary skill in the art, and includes exemplary dosage amounts for a mammal of from about 0.05 to 100 mg/kg of body weight of active compound per day, which can be administered in a single dose or in the form of individual divided doses, such as from 1 to 4 times per day. Preferred subjects for treatment include animals, most preferably mammalian species such as humans, and domestic animals such as dogs, cats, horses, and the like.

The compounds of the invention, and pharmaceutically acceptable salts thereof, also embrace prodrugs, pharmaceutically acceptable salts of such prodrugs, and other bioequivalents. Prodrugs and solvates of the inventive compounds are also contemplated. As will be appreciated by the skilled practitioner, prodrugs are suitable for use in the methods according to the present invention. Such prodrugs are preferably administered orally since hydrolysis in many instances occurs principally under the influence of the digestive enzymes. Parenteral administration can be used where the ester per se is active, or in those instances where hydrolysis occurs in the blood. Examples of physiologically hydrolyzable esters of compounds of formula (I) include C1–6alkylbenzyl, 4-methoxybenzyl, indanyl, phthalyl, methoxymethyl, $C_{1-6}$ alkanoyloxy-C1–6alkyl, e.g. acetoxymethyl, pivaloyloxymethyl or propionyloxymethyl, C1–6alkoxycarbonyloxy-C1–6alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters can be prepared by conventional techniques known in the art.

The inventive compounds and compositions can be employed alone or in combination with each other and/or other suitable therapeutic agents useful in treating NF-κB and TNF-α associated conditions. Exemplary of such other therapeutic agents include corticosteroids, rolipram, calphostin, CSAIDs, 4-substituted imidazo[1,2-A] quinoxalines as disclosed in U.S. Pat. No. 4,200,750 and Ceccarelli et al., supra; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathiprine and cyclophosphamide; TNF-α inhibitors such as tenidap, anti-TNF antibodies or soluble TNF receptor, and rapamycin (sirolimus or Rapamune) or derivatives thereof; and other cancer drugs and treatments, including radiation treatments and daunorubicin.

The above other therapeutic agents, when employed in combination with the compounds of the present invention, can be used, for example, in those amounts indicated in the Physicians' Desk Reference (PDR) or as otherwise determined by one of ordinary skill in the art.

It should be understood that one skilled in the field is able to make various modifications to the compounds, compositions and schemes described above, applying the ordinary level of skill in the field, without departing from the spirit or scope of the invention. All such modifications are intended to be included within the invention as defined in the appended claims.

EXAMPLES

The Examples below are provided to illustrate the subject invention and are not intended to limit the invention.

Example 1

Method of Preparation of IKK Inhibitor 4(2'-aminoethyl)amino-1,8-dimethyl—imidazo(1,2-a)quinoxaline (Compound 6)

The IKK inhibitory compound 4(2'-aminoethyl)amino-1,8-dimethylimidazo(1,2-a)quinoxaline, or compound 6 newly described herein, can be prepared by a method as described in the following scheme. Starting materials are commercially available or can be readily prepared by one of ordinary skill in the art, and/or modifications can be made to the method of the scheme by one skilled in the art, using known methods and practices.

Chemical Scheme for Preparing Compound 6

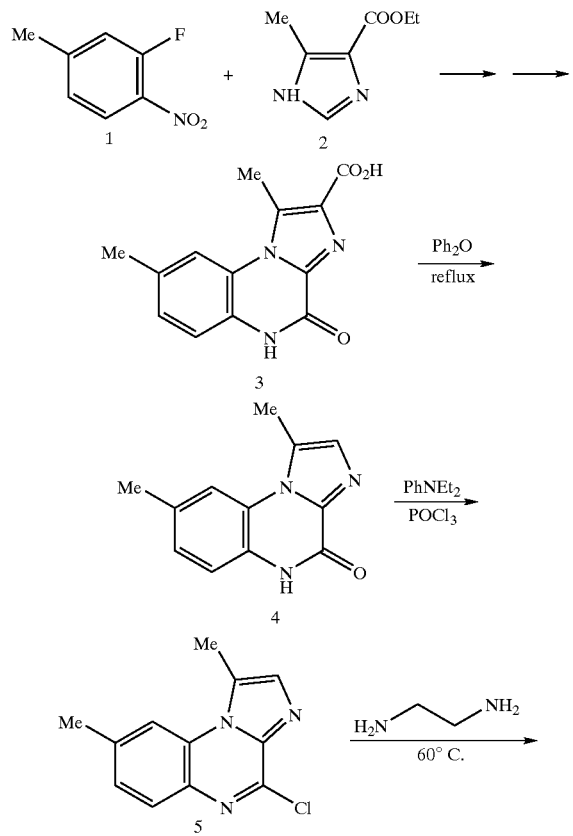

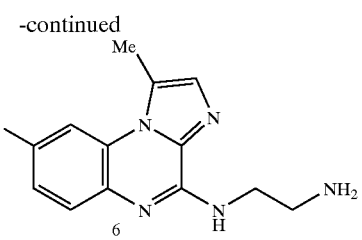

Compound 6 or 4(2'-aminoethyl)amino-1,8-dimethylimidazo(1,2-a)quinoxaline, can be prepared as shown in the above scheme: 3-fluoro-4-nitrotoluene (compound 1) is reacted with ethyl 5-methylimidazole-4-caboxylate (compound 2) according to known procedures to produce, after several steps, the imidazoquinoxalone-2-carboxylic acid (compound 3). Upon decarboxylation of said acid (compound 3) in a high-boiling solvent, such as diphenyl ether ($Ph_2O$), 1,8-dimethylimidazoquinoxalone (compound 4) is produced. Compound 4 is then chlorinated using standard reagents, such as phosphorus oxychloride ($POCl_3$) and N,N-diethylaniline ($PhNEt_2$) to give 4-chloro-1,8-dimethylimidazoquinoxaline (compound 5). Compound 5 is then condensed with 1,2-diaminoethane or ethylenediamine to produce the final compound 4(2'-aminoethyl)amino-1,8-dimethylimidazo(1,2-a)quinoxaline (compound 6).

Preparation of Reagents and Starting Materials for Compound 6

3-fluoro-4-nitrotoluene (Compound 1)

Compound 1 is commercially available from Aldrich Chemical Company (Milwaukee, Wis.).

Ethyl 5-methylimidazole-4-carboxylate (Compound 2)

Compound 2 is commercially available from Aldrich Chemical Company (Milwaukee, Wis.).

Preparation of Imidazoquinoxalone-2-carboxylic acid (Compound 3)

Compound 1 and compound 2 are reacted to give, after several steps, compound 3, following the procedure of Trieber et al. (German Offen. 4,329,970 (Oct. 6, 1994)).

Preparation of 4,5-Dihydro-1,8-dimethylimidazo(1,2-a)quinoxalin-4-one (Compound 4)

A suspension of 4,5-dihydro-1,8-dimethylimidazo(1,2-a)quinoxalin-4-one-2-carboxylic acid (compound 3) (32 g, 124 mmol) in diphenyl ether (400 mL) was refluxed at 260° C. for 2 hours. After the suspension cooled down to room temperature, hexanes ($C_6H_{14}$; 500 mL) were added to further precipitate the product. The solid was filtered, giving the title compound 4 as a white solid (29.6 g). $^1H$ nuclear magnetic resonance, NMR (500 MHz, hexadeuteriodimethylsulfoxide, $d_6$-DMSO) δ 11.7 (s, 1H), 7.91 (s, 1H), 7.31 (s, 1H), 7.29 (d, J=8.1 Hz, 1H), 7.22 (d, J=8.3 Hz, 1H), 2.81 (s, 3H), 2.41 (s, 3H); MS (ESI), m/z 214.13 [(M+H)$^+$; calculated for compound 4, $C_{12}H_{11}N_3O$:213.09].

Preparation of 4-chloro-1,8-dimethylimidazo(1,2-a)quinoxaline (Compound 5)

A mixture of 4,5-dihydro-1,8-dimethylimidazo(1,2-a)quinoxalin-4-one (compound 4) (29.6 g, 139 mmol) and N,N-diethylaniline ($PhNEt_2$, 45 mL) was refluxed in phosphorus oxychloride ($POCl_3$; 250 mL) for 1 hour. The solvent was evaporated under vacuum; the residue was diluted with chloroform, $CHCl_3$ (1000 mL), followed by careful neutralization with cold saturated sodium carbonate, ($Na_2CO_3$) solution. The aqueous layer was further extracted with $CHCl_3$. The combined organic layer was dried over magnesium sulfate ($MgSO_4$) filtered and concentrated. Flash chromatography using ethyl acetate and hexanes (EtOAc/Hexanes, 60/40) provided the title compound 5 as a white solid (25 g). $^1$H NMR (500 MHz, CDCl$_3$) δ 8.07 (s, 1H), 7.93 (d, J=8.3 Hz, 2H), 7.54 (d, J=0.7 Hz, 1H), 7.41 (dd, J=8.4, 1.2 Hz, 1H), 2.97 (s, 3H), 2.59 (s, 3H); MS (ESI), m/z 232.04 [(M+H)$^+$; calculated for compound 5, C$_{12}$H$_{10}$ClN$_3$: 231.06].

Preparation of 4(2'-Aminoethyl)amino-1,8-dimethylimidazo (1,2-a) quinoxaline (Compound 6)

A solution of 4-chloro-1,8-dimethylimidazo(1,2-a) quinoxaline (compound 5) (4.8 g, 21 mmol) in ethylenediamine (300 mL) was heated at 60° C. under nitrogen gas (N$_2$) for 16 hours. The solvent was evaporated under vacuum. The residue was diluted with EtOAc (200 mL), washed with saturated Na$_2$CO$_3$ and brine, dried over MgSO$_4$, filtered and concentrated. Flash chromatography using methanol (MeOH) provided a solid, which was then dissolved with CHCl$_3$ and filtered to remove any dissolved silica gel. The filtrate was concentrated under vacuum, providing the title compound 6 as a white solid (4.67 g). $^1$H NMR (500 MHz, CDCl$_3$) δ 7.88 (s, 1H), 7.63 (d, J=8.3 Hz, 1H), 7.26 (s, 1H), 7.22 (d, J=8.3 Hz, 1H), 6.31 (s, 1H), 3.63 (apparent q, J=5.9 Hz, 2H), 2.96 (t, J=6.0 Hz, 2H), 2.88 (s, 3H), 1.38 (br, 2H); MS (ESI), m/z 256.15 [(M+H)$^+$; calculated for compound 6, C$_{14}$H$_{17}$N$_5$:255.15].

Preparation of HCl Salt of 4(2'-Aminoethyl)amino-1,8-dimethylimidazo(1,2-a) quinoxaline (Compound 6)

Compound 6 or 4(2'-Aminoethyl)amino-1,8-dimethylimidazo(1,2-a)quinoxaline (4.67 g, 18.3 mmol) was dissolved with aqueous hydrochloric acid, HCl (1.0 N, 18.3 mL) and water, H$_2$O (50 mL) at room temperature. Subsequent removal of water using a lyophilizer provided the hydrochloride salt as a white solid (5.22 g). The hydrochloride salt of compound 6 is preferred in the described methods although other salts, e.g. acetate, sulfate, citrates, as well as the free base of compound 6, are also suitable for use.

In Examples 2–7, a salt form of 4(2'-Aminoethyl)amino-1,8-dimethylimidazo(1,2-a)quinoxaline was used.

Example 2

Analysis of Inhibitory Potential of IKK Inhibitors, Using 4(2'-Aminoethyl)amino-1,8-dimethylimidazo (1,2-a)quinoxaline (Compound 6)

IKK-1/IKK-2 Enzyme Assay

Assays for measuring the inhibitory potential of test compounds, specifically compound 6, (4(2'-aminoethyl)amino-1,8-dimethylimidazo(1,2-a)quinoxaline), against IKK activity employed $^{33}$P-labeled ATP and a recombinant IκB-α as substrates. In this assay, test compound was added to a solution of 0.5 mM IκB-α in 40 mM Tris-HCl, pH 8, containing 4 mM MgCl$_2$, 1 mM dithiothreitol, and 2 mM $^{33}$P-labeled ATP. IKK enzyme (either the multisubunit complex from HeLa cells, recombinantly expressed IKK-1, or recombinantly expressed IKK-2) was then added to initiate the reaction. The multisubunit complex was isolated according to the procedure of Lee et al. [(1997) Cell 88:213–222] or Mercurio et al. [(1997) 278:860–866]. The recombinant IKK-1 and IKK-2 were expressed using the procedure of Burke et al. [(1999) J. Biol. Chem. 274:36146–36152]. After incubating for 10 minutes at 30° C., the reaction was quenched by the addition of EDTA to a final concentration of 30 mM. In order to separate the phosphorylated IκB-α (Santa Cruz Biotechnology; Santa Cruz, Calif.) product from unreacted ATP, sodium dodecylsulfate polyacrylamide gel electrophoresis (SDS-PAGE) was performed. Phosphoimager analysis of the amount of $^{33}$P incorporation into IκB-α was executed using a Molecular Dynamics 445 Phosphoimager, and the inhibition of IKK activity by the test compound was calculated from control samples containing no inhibitor. The IC$_{50}$ is defined as the concentration of test compound which produces 50% inhibition of IKK activity.

The results presented in Table 1 show the inhibition of IKK activity using $^{33}$P-labeled ATP and IκB-α as substrates for recombinantly expressed IKK-1 and IKK-2, wherein a test compound concentration of 5 μM and 0.5 μM, respectively, was shown to achieve inhibition of IKK activity by 50%. The IKK inhibitor, compound 6, inhibits IKK-2 at an IC$_{50}$ which is 10 fold less than that necessary to inhibit IKK-1 by 50%. As presented in Table 1, compound 6 inhibits IKK-2 with greater effectiveness than IKK-1, thus demonstrating a selectivity of this compound for IKK-2 inhibition over IKK-1.

TABLE 1

| Test Compound | IKK-1 IC$_{50}$ | IKK-2 IC$_{50}$ |
| --- | --- | --- |
| Compound 6 | 5 μM | 0.5 μM |

Example 3

Pharmacokinetics of Compound 6 in Mice

Compound 6 was administered to BALB/c mice either per orally (p.o.) or intravenously (i.v.). Blood was drawn at various times (0.5 to 4 hours) after dosing and the plasma drug levels measured by liquid chromatography-mass spectral analysis. An oral bioavailability of 100% for compound 6 was calculated from the area under the curve (AUC) derived from a plot of plasma levels versus time after the p.o. dose, and then dividing by the AUC from the i.v. dose. An i.v. half-life of 7.9 hours was calculated from the apparent terminal elimination phase after the i.v. dose. Generally, to be considered, oral bioavailability ranges from about 10% to about 100%, more preferably from about 50% to about 100%, and most preferably from 80% to about 100%.

Example 4

Measurement of Median Survival Time of transplanted Hearts in BALB/c Mice

Murine Neonatal Heart to Ear Transplants

Cardiac transplants were performed as described by Fulmer et al. (Fulmer, R. I. et al. The American Journal of Anatomy 113:273–281, 1963). Neonatal hearts were obtained from newborn C57BL/6 mice not more than 48 hours after birth. The hearts were transplanted into recipient BALB/c mice, which were prepared under anesthesia by making a small incision at the base of the ear pinna and forming a pocket by gently lifting the skin away from the ear. The incision permitted the insertion of the donor heart subcutaneously into the pocket. Post-operatively, the cardiac tissue typically does not begin to beat until 3 to 5 days after transplantation until vascular connections are established. The pulsations of the heart were measured by contractile activity with an appropriate electrocardiogram (ECG) monitoring device. The contractile activity of the transplanted graft was monitored daily. The time of graft rejection was defined as the day after transplantation on which contractile activity ceased. Without therapeutic intervention, the host mounts an immune response to the transplanted heart (i.e., graft rejection). This immune response causes the transplanted heart to cease beating typically 10–14 days post transplantation.

Test compounds were administered in daily doses either alone or in combination with other therapies, such as Cyclosporine A (15 mg/kg, orally, "p.o.") or CTLA4-Ig (200 µg in 200 µl PBS given intraperitoneally on only days 0, 2, and 4). Table 2 presents the effects of test compounds on median survival time of transplanted hearts, either alone or in combination with Cyclosporine A (CsA). Table 3 presents the effects of test compounds on median survival time of transplanted hearts, either alone or in combination with CTLA4-Ig.

TABLE 2

| Test Compound | Median Graft Survival Time | Statistical Significance |
|---|---|---|
| Vehicle (water) | 12 days | |
| Cyclosporine A, 15 mg/kg, p.o. | 14 days | |
| Compound 6, 50 mg/kg, p.o. | 12 days | |
| Cyclosporine A, 15 mg/kg, p.o. Plus Compound 6, 50 mg/kg, p.o. | 29 days | $P < 0.01$ vs. vehicle, $P < 0.01$ vs. CsA alone |

TABLE 3

| Test Compound | Median Graft Survival Time | Statistical Significance |
|---|---|---|
| CTLA4-Ig Plus Compound 6, 50 mg/kg, p.o. | 32 days | $P < 0.01$ vs. vehicle, $P = 0.02$ vs. CTLA4-Ig alone |
| CTLA4-Ig Plus Compound 6, 100 mg/kg, p.o. | >60 days | $P < 0.01$ vs. vehicle, $P < 0.01$ vs. CTLA4-Ig alone |

The synergistic effects between compound 6 and either cyclosporine A or CTLA4-Ig indicate that an IKK inhibitor is highly efficacious in the in vivo treatment of solid organ transplant rejection particularly when co-administered with other immunosuppressive agents. Because these agents are not completely effective when administered alone, transplant patients typically receive a "cocktail" of immunosuppressive agents.

Example 5

Effect of IKK Inhibitor 4(2'-Aminoethyl)amino-1,8-dimethylimidazo(1,2-a)quinoxaline (Compound 6) on Disease Incidence in the Murine Model of Collagen-induced Arthritis Collagen-induced Arthritis The murine model of collagen-induced arthritis is widely used to study disease mechanisms and potential therapies for rheumatoid arthritis in humans (Staines et al., Br. J. Rheumatol. 33:798–807, 1994; Feldmann et al., Annu. Rev. Immunol. 14:397–440, 1996).

DBA/1 LacJ male mice 6–8 wk (Jackson Laboratories; Bar Harbor, Me.) were immunized subcutaneously on day 0 and on day 21 with 100 µg bovine type 11 collagen in 0.1 mL RIBI Adjuvant System (RAS) with monophosphoryl lipid A(RIBI lmmunoChem Research; Hamilton, Mont.). In this model, disease onset occurs within one week after the second collagen injection.

When treated in a preventative mode, test compounds were administered daily beginning on day 0 through day 41. FIG. 1 shows a graph of the percentage of mice within each treatment group (6–10 animals per group) which show any sign of disease regardless of severity. Administration of 4(2'-aminoethyl)amino-1,8-dimethylimidazo(1,2-a) quinoxaline (compound 6) at a concentration of 100 mg/kg, resulted in a significant difference in incidence of disease compared with vehicle alone.

In the established (i.e. therapeutic) mode, the administration of test compounds was initiated only after paw inflammation of an animal had achieved a score of 2 (as defined below), at which time, the animal was randomly assigned to a treatment group. Treatment continued daily for all four paws as described below.

Following the Day 21 booster, mice were regularly monitored for the development and severity of paw inflammation. Each paw was visually scored by the following clinical scoring scheme as presented in Table 4:

TABLE 4

| Score | Description |
|---|---|
| 0 | Normal |
| 1 | One (or more) joints inflamed on digits |
| 2 | Plantar surface of paw inflamed and paw thickness increased |
| 3 | Ankylosis (significantly reduced hock joint motion on flexion/extension) |

Clinical paw scores for all four paws were summed for each mouse and the mean ± standard deviation (SD) was calculated for each treatment group. The incidence of disease is defined as the percent of animals within a treatment group which showed any sign of disease regardless of severity.

Histological scoring involved evaluating histologically and grading semi-quantitatively tibiotarsal joints of sacrificed mice, specifically examining the severity of inflammation, synovial hyperplasia, bone resorption, and cartilage erosion. Cumulative arthritis injury scores for each group were compared by the nonparametric Kruskal-Wallis analysis of variance.

Figure 2:
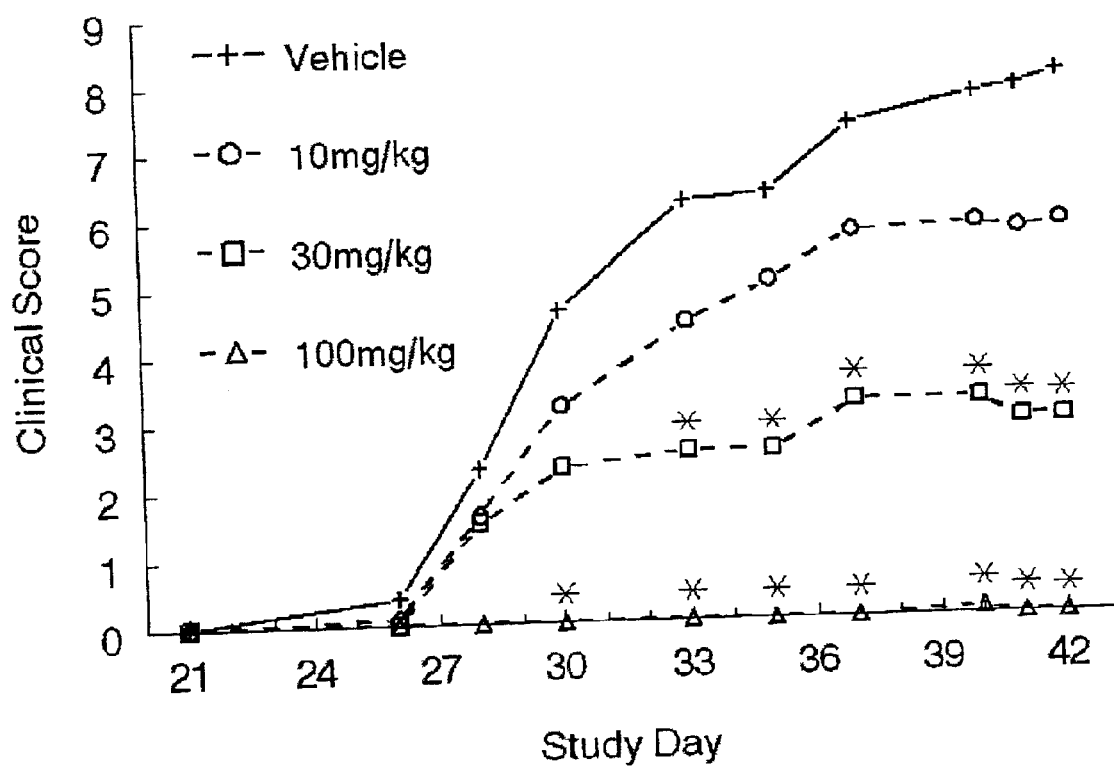
FIG. 2 shows the effect of 4(2'-aminoethyl)amino-1,8-dimethylimidazo(1,2-a)quinoxaline (compound 6) on the average gross clinical score for all mice within each treatment in the murine model of collagen-induced arthritis based on clinical scores corresponding to the study day. The test compound was administered once daily in the preventative dosing mode. *$p<0.05$, Mann-Whitney U-test.

FIG. 2 shows the average gross clinical score for all mice within each treatment in the collagen-induced arthritis murine model as determined on each study day. The test compound was administered once daily in the preventative dosing mode. Table 5 presents the histological evaluation of the effect of 4(2'-aminoethyl)amino-1,8-dimethylimidazo(1,2-a) quinoxaline (compound 6) on the cumulative arthritis injury scores ± standard error mean (sem) upon sacrificing the animals at the end of the study in the murine model of collagen-induced arthritis. Administration of 4(2'-aminoethyl)amino-1,8-dimethylimidazo(1,2-a)quinoxaline (compound 6) at concentrations of 30 and 100 mg/kg resulted in histological cumulative arthritis injury scores of 0.4 and 0, which parallels the results depicted in FIG. 2.

Preventative Mode

TABLE 5

| Treatment | Cumulative arthritis injury score (±sem) | Statistical Significance* |
|---|---|---|
| Vehicle (water) | 4.4 ± 1.5 | |
| Compound 6, 10 mg/kg | 5.3 ± 1.7 | |
| Compound 6, 30 mg/kg | 0.4 ± 0.4 | $P = 0.02$ |
| Compound 6, 100 mg/kg | 0.0 | $P = 0.004$ |

*vs. vehicle-treated group.

Figure 3:
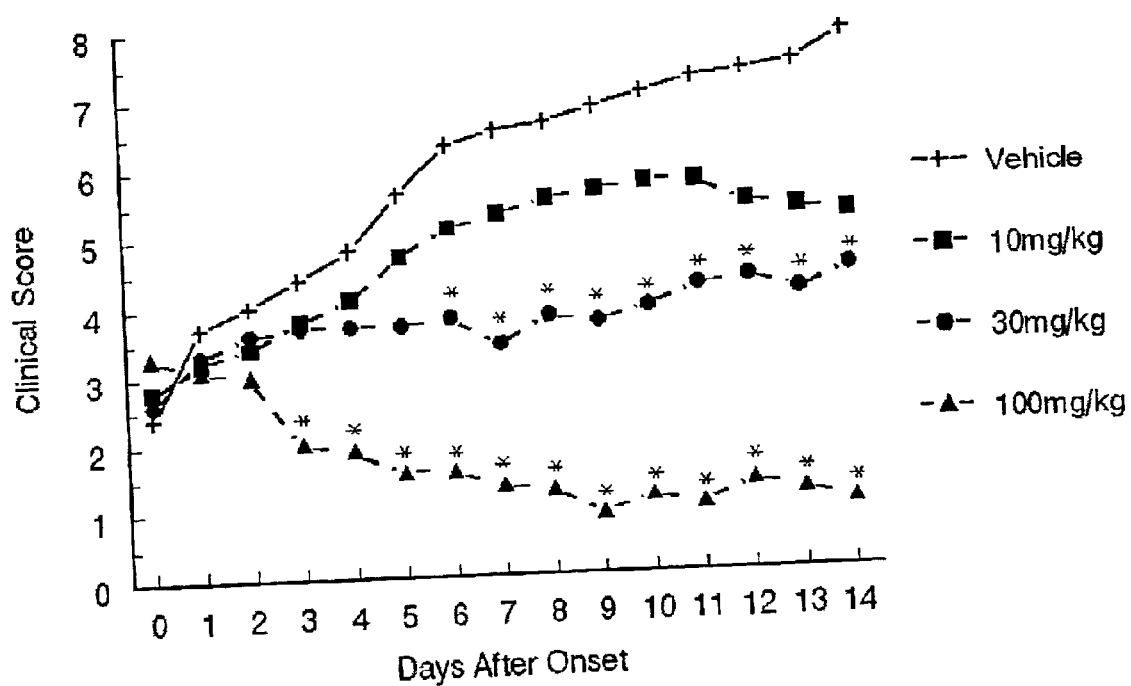
FIG. 3 shows the effect of 4(2'-aminoethyl)amino-1,8-dimethylimidazo(1,2-a)quinoxaline (compound 6) on disease incidence in the murine model of collagen-induced arthritis based on the clinical score corresponding to the days after disease onset. The test compound was administered once daily in the established disease dosing mode. *$p<0.05$, Mann-Whitney U-test.

FIG. 3 shows the effects of 4(2'-aminoethyl)amino-1,8-dimethylimidazo(1,2-a)quinoxaline (compound 6) administered in the established disease mode (i.e., after disease onset) on the average gross clinical score for all mice within each treatment in the murine model of collagen-induced arthritis as determined on the days following disease onset.

Table 6 presents the histological evaluation of the effect of 4(2'-aminoethyl)amino-1,8-dimethylimidazo(1,2-a)

quinoxaline (compound 6) on the cumulative arthritis injury scores in the established disease mode of murine model of collagen-induced arthritis two weeks after disease onset.

Established Mode

TABLE 6

| Treatment | Cumulative Arthritis Injury Score (±sem) | Statistical significance* |
|---|---|---|
| Vehicle (water) | 7.0 ± 0.5 | |
| Compound 6, 10 mg/kg | 4.2 ± 1.0 | P = 0.028 |
| Compound 6, 30 mg/kg | 2.1 ± 0.9 | P = 0.004 |
| Compound 6, 100 mg/kg | 0.9 ± 0.5 | P = 0.001 |

*vs. vehicle-treated group.

The murine model of collagen-induced arthritis shares many of the same biochemical and pathological mechanisms as does rheumatoid arthritis in humans, and was used for preventing and treating arthritis upon the administration of 4(2'-aminoethyl)amino-1,8-dimethylimidazo(1,2-a) quinoxaline (compound 6). FIGS. 1 and 2 and Table 5 show that daily administration of 30 mg/kg (p.o.) of compound 6 inhibited disease onset, and that 100 mg/kg (p.o.) of compound 6 prevented any disease onset when dosed in a preventative mode. When the IKK inhibitor was administered after disease onset (i.e., established mode of therapy), FIG. 3 and Table 6 show that treatment with 30 mg/kg (p.o.) of compound 6 significantly inhibited disease progression when compared with vehicle treated animals, while a dose of 100 mg/kg (p.o.) of compound 6 actually led to significant disease resolution. These results support the advantages provided by the present invention in which inflammatory diseases or disorders, such as rheumatoid arthritis, are prevented or ameliorated by inhibiting IKK activity.

Example 6

Effect of IKK Inhibitor 4(2'-Aminoethyl)amino-1,8-dimethylimidazo(1,2-a)Quinoxaline on Disease Incidence in the Murine Model of Dextran Sulfate Sodium-induced Inflammatory Bowel Disease Dextran Sulfate Sodium-Induced Murine Model of Inflammatory Bowel Disease Dextran sulfate sodium (DSS)-induced colitis in mice shows several of the same pathological mechanisms of inflammatory bowel disease (IBD) as it presents in humans, and has been used to study various treatments (Okayasu et al., Gastroenterology 98:694–702, 1990; Axelsson et al., Aliment. Pharmacol. Ther. 12:925–934, 1998). The mouse models are used as predictors of IBD in humans and to develop effective treatments for human use.

In this model, Swiss-Webster mice (8 weeks old, 5 animals per treatment group) were given 6% DSS in their drinking water for 7 consecutive days to induce intestinal inflammation. Test compounds were administered daily throughout the study. On day 9, animals were sacrificed and the colons were removed for clinical and histological evaluation.

Clinical scoring was determined by the gross clinical evaluation of the injury on a scale from 0 (normal) to 3 (severe) as detailed in Table 7.

TABLE 7

| Score | Description |
|---|---|
| 0 | Normal |
| 1 | Relatively normal colon length, slight thickening of tissue. |
| 2 | Shortened colon length, thick along entire length of colon with loss of striations. Some areas of redness. |
| 3 | Considerably shortened length with very thick tissue containing areas of raised lesions. |

For histological scoring, colon sections were graded as to the severity of crypt injury and the degree of inflammation. The crypt injury was scored as detailed in Table 8, wherein the crypt is part of the glandular make-up of the colon.

TABLE 8

| Score | Description |
|---|---|
| 0 | Normal; intact crypt |
| 1 | Loss of basilar - one-third of the crypt |
| 2 | Loss of basilar - two-thirds of the crypt |
| 3 | Loss of the entire crypt with surface epithelium intact |
| 4 | Loss of the entire crypt with epithelial erosion |

Tissue involvement was scored as detailed in Table 9. Any signs of crypt injury or inflammation, regardless of severity, constitute tissue involvement.

TABLE 9

| Score | Description |
|---|---|
| 0 | No involvement |
| 1 | 1–25% involvement |
| 2 | 26–50% involvement |
| 3 | 51–75% involvement |
| 4 | 76–100% involvement |

The injury histological score is defined as the product of the crypt injury grade and the tissue involvement grade. The scoring of severity of inflammation is detailed in Table 10.

TABLE 10

| Score | Description |
|---|---|
| 0 | Normal; non-remarkable |
| 1 | Minimal |
| 2 | Mild |
| 3 | Moderate |
| 4 | Severe |

The inflammation histological score is the product of the severity of inflammation grade and the extent of tissue involvement grade. Crypt injury and inflammatory scoring were performed on each colon section and a mean score and standard error were determined for each section. Cumulative crypt injury and inflammatory scores for each group were determined. Table 11 presents the clinical scores of colons in mice with DSS-induced colitis. The results of Table 12 present the cumulative injury and inflammation scores of colons in mice with DSS-induced colitis.

TABLE 11

| Treatment | Mean clinical score |
|---|---|
| UNTREATED | 2.50 ± 0.45 |
| COMPOUND 6, 30 mg/kg, p.o. | 1.10 ± 0.49* |
| COMPOUND 6, 100 mg/kg, p.o. | 1.00 ± 0.35* |

*Statistical significance vs. untreated group, P < 0.05

TABLE 12

| Treatment | Group Mean Injury Histological Score | Group Mean Inflammation Histological Score |
|---|---|---|
| UNTREATED | 8.52 ± 0.81 | 12.33 ± 0.40 |
| COMPOUND 6, 30 mg/kg, p.o. | 4.83 ± 0.55* | 7.58 ± 0.81* |
| COMPOUND 6, 100 mg/kg, p.o. | 5.66 ± 0.87* | 6.82 ± 0.85* |

*Statistical significance vs. untreated group, P < 0.05

The results show that 4(2'-aminoethyl)amino-1,8-dimethylimidazo(1,2-a)quinoxaline (compound 6) prevented and treated IBD in the well-established murine model of inflammatory bowel disease (IBD) in humans. Tables 11 and 12 show that daily administration of the IKK inhibitor (compound 6) resulted in a statistically significant decrease in clinical and histological score when compared with untreated mice. Such results support the advantageous outcome afforded by the present invention in which inhibition of the IKK enzyme prevents and/or ameliorates inflammatory diseases and disorders such as IBD.

Example 7

Effect of IKK Inhibitor 4(2'-Aminoethyl)amino-1,8-dimethylimidazo(1,2-a)quinoxaline on Disease Incidence in the Murine Model of Ovalbumin-induced Inflammatory Cell Infiltration in the Lung of Sensitized Mice Inflammatory Cell Infiltration into the Lung of Ovalbumin-challenged Mice Pulmonary inflammation with infiltration of eosinophils and other inflammatory cells is a hallmark of asthma and other allergic respiratory disorders. To determine whether an IKK inhibitor was efficacious in the in vivo treatment of respiratory disorders which afflict many patients, test compounds were administered in a murine model of pulmonary inflammation similar to that described by Kung et al. (Kung, T. T. et al., Int. Arch. Allergy Immunol. 105:83–90, 1994).

In the pulmonary inflammation animal model, BALB/c mice were sensitized by an intraperitoneal injection of 0.1 mL alum-precipitated antigen containing 40 μg ovalbumin adsorbed to aluminum hydroxide gel on days 0 and 10. On day 14, animals received intranasal challenge with 100 μg ovalbumin in 50 μl saline (PBS). Mice were injected intraperitoneally with antigen to sensitize the animals prior to intranasal challenge to induce lung inflammation. Administration of the test compound was given on days 14 to 17. On day 18, bronchoalveolar lavage fluid (BAL) was collected for measurements of total inflammatory cell infiltration (eosinophils, monocytes, lymphocytes, and neutrophils). Table 13 presents the effect of 4(2'-aminoethyl)amino-1,8-dimethylimidazo(1,2-a)quinoxaline (compound 6) on ovalbumin-induced inflammatory cell infiltration into the lungs of sensitized mice after daily administration of compound.

TABLE 13

| Test Compound | Total Inflammatory Cells in BAL | Statistical Significance vs. Vehicle Control |
|---|---|---|
| Vehicle (water) | $5.8 \times 10^6 \pm 1.2 \times 10^6$ | |
| Compound 6, 30 mg/kg, p.o. | $2.8 \times 10^6 \pm 1.3 \times 10^6$ | P = 0.13 |
| Compound 6, 100 mg/kg, p.o. | $2.2 \times 10^6 \pm 0.3 \times 10^6$ | P = 0.02 |

*Statistical significance vs. untreated group, P < 0.05

Ovalbumin-induced inflammatory cell infiltration in murine lung provides a model system for pulmonary inflammation, specifically asthma and other allergic respiratory disorders in humans. Compound 6, 4(2'-aminoethyl)amino-1,8-dimethylimidazo(1,2-a)quinoxaline, was administered in a murine model of pulmonary inflammation for the treatment of inflammation and immune-related conditions. The results presented in Table 13 show that administration of compound 6 after ovalbumin challenge to sensitized mice resulted in a statistically significant decrease in total inflammatory cells in the lungs, as determined by measurements from bronchoalveolar lavage fluid when compared with untreated mice. These results support the advantages provided by the present invention in which inflammatory diseases or disorders, such as asthma and chronic obstructive pulmonary disease, are ameliorated by inhibiting IKK activity.

Example 8

TNFα Production Assay

THP-1 (human monocytic cell line) obtained from ATCC was cultured in RPMI-1640 supplemented with 10% FBS, sodium pyruvate, HEPES, 2-mercaptoethanol, Penicillin/Streptomycin. To a 96-well plate containing THP-1 cells ($1.4 \times 10^6$/mL, $2.5 \times 10^5$ cells/well) in 180 μL RPMI-1640 was added 20 μL of the test compound in 10% DMSO. Typically, test compound concentrations of 0.1–100 μM were used in the assay. After one hour at 37° C., 20 μL of 1000 ng/mL lipopolysaccharide (LPS from Salmonella typhosa, Sigma) was added to each well. After an additional 6 hours at 37° C., the supernatants were collected following a 5 minute centrifugation of the plate to pellet the cells. The amount of TNFα in these supernatants was then measured using a TNFα-specific ELISA (Pharmingen). After subtracting out the amount of TNFα in a control that had not been treated with LPS, the percent inhibition was calculated versus a control that was treated with LPS but with no test compound added. $IC_{50}$ values were calculated from the percentage inhibition at various doses. In the TNF-α production assay, compound 6 was determined to have an $IC_{50}$ of 4 μM. Compounds of Examples 12–19 demonstrated $IC_{50}$ values of below 9 μM, with preferred and more preferred compounds having $IC_{50}$ values of below 2 μM and 1 μM, respectively, in this assay.

Example 9

TNFα-Stimulated Degradation of IκBα in THP-1 Cells

TNFα stimulation of monocytic THP-1 cells leads to the proteolytic degradation of IκBα. Both an IKK-dependent phosphorylation and ubiquitin ligase-dependent ubiquitination of IκBα are essential steps in the TNFα-stimulated pathway targeting IκBα for proteolytic degradation by the proteosome.

THP-1 cells were suspended in RPMI -1640 supplemented with 10% fetal bovine serum, preincubated for 60 mins with test agent, then stimulated for 15 mins with TNFα (100 ng/mL, R&D Systems). Total cell lysates were fractionated by sodium dodecylsulfate-polyacrylamide electrophoresis followed by Western blot analysis. IκBα was detected using a polyclonal antibody from Santa Cruz (catalog #sc-4094) and ECL reagents (Amersham). Films were scanned using a Kodak ID Image Analysis system to quantitate the amount of IκBα. Compounds of formula (I) demonstrated up to 100% inhibition of the TNFα-induced degradation of IκBα in THP-1 cells at 10 μM. In the IκB degradation assay, compound 6 had an $IC_{50}$ of 5 μM upon measuring the TNFα-induced degradation of IκBα in THP-1.

Example 10

LPS-induced Serum TNFα in Mice

As a measure of activity against NF-κB-dependent TNFα production in vivo, test compounds were administered to BALB/c mice subsequently challenged with an intravenous dose of *E. coli* LPS (1 μg in 100 μL phosphate-buffered saline). One hour after LPS challenge, blood was collected from the mice and the levels of TNFα in the serum measured by EIA(R&D Systems). Inhibition was calculated from control animals which received LPS challenge with no test compound. Compounds of formula (I) demonstrated inhibition of the LPS-induced serum TNFα levels in vivo in the range of about 30 to 65% at 10 mg/kg, p.o; in the range of about 70 to 90% at 30 mg/kg, p.o.; and in the range of above 90% at 100 mg/kg p.o. Compound 6 demonstrated inhibition of the LPS-induced serum TNF. levels in vivo in the range of about 27–63% at 10 mg/kg, p.o.; in the range of about 53–89% at 30 mg/kg, p.o.; and in the range of about 83–92% at 50 mg/kg, p.o.

Accordingly, compounds of formula (I) have been tested and shown activity as inhibitors of TNF-α and the NF-κB pathway.

Example 11

Methods of Preparation Related to Formula(I) Compounds

The inventive compounds of formula (I) can be prepared by methods such as those illustrated in the following Schemes I to V in this example. Starting materials are commercially available or can be readily prepared by one of ordinary skill in the art, and/or modifications can be made to the methods of Schemes I to V by one skilled in the art, using known methods. For all of the schemes and compounds, the groups $R_1$, $R_2$, $R_3$ and $R_4$ are as described herein for a compound of formula (I), unless otherwise indicated, and appropriate starting materials can be selected by one skilled in the field having the desired groups $R_1$, $R_2$, $R_3$ and $R_4$. Groups designated R', as well as solvents, temperatures, pressures, and other reaction conditions, can be selected by one of ordinary skill in the art. For example, in these schemes chlorinating agents can include phosphorous oxychloride, catalytic agents can include metals such as Pd, and solvents can be selected from 1,2-dichlorobenzene, methylene chloride, DMF, THF, alcohols, ethers, dioxane, acetonitrile, water, mixtures of ethers and water, and the like.

Abbreviations
For ease of reference the following abbreviations are used in the schemes and Examples herein:

| | |
|---|---|
| Me = methyl | Et = ethyl |
| MeOH = methanol | EtOH = ethanol |
| i-PrOH = isopropanol | Ph = phenyl |
| Bz = benzyl | DCM = dichloromethane |
| DMF = dimethyl formamide | DMSO = dimethyl sulfoxide |
| NaOH = sodium hydroxide | TEA or $Et_3N$ = triethylamine |
| TFA = trifluoroacetic acid | THF = tetrahydrofuran |
| $K_2CO_3$ = potassium carbonate | $Na_2S_2O_3$ = sodium thiosulfate |
| min = minute(s) | L = LITER |
| mL = milliliter | μL = microliter |
| G = GRAM(S) | mg = milligram(s) |
| mol = moles | mmol = millimole(s) |
| meq = milliequivalent | RT = room temperature |
| sat or sat'd = saturated | aq. = aqueous |
| TLC = thin layer chromatography | HPLC = high performance liquid chromatography |
| LC/MS = high performance liquid chromatography/mass spectrometry | MS = mass spectrometry |
| NMR = nuclear magnetic resonance | mp = melting point |

Definitions of Terms Used in the Reaction Schemes in Example 11

The following are definitions of terms used herein and in the reaction schemes.

"Acetal, ketal, thioacetal or thioketal formation" are processes known in the art and illustrated in "Protective Groups in Organic Synthesis", Second Ed., T. W. Green and P. G. W. Wuts, John Wiley & Sons, New York, 1991, Chapter 4 and references therein, incorporated herein by reference.

"Acid halide formation" includes methods of converting a carboxylic acid to an acid halide. For example, this reaction can be performed with thionyl chloride, oxalyl chloride or bromide in the presence of DMF in DCM and phosphorus trichloride or tribromide.

"Alkylation" includes all alkylation procedures such as alkylation of desired alcohol or ketone groups by treatment with organic or inorganic base in an appropriate organic solvent, followed by addition of an alkylating agent such as an alkyl, allyl or benzyl halide, mesylate or tosylate to the generated enolate, phenolate or thiophenolate.

"Aromatic substitution" includes all aromatic substitution methods known in the field including nucleophilic substitutions of aromatic halides by water in presence of sulfuric acid or trifluoroacetic acid, or by alkoxides, aryloxides, thioalkoxides or thioaryloxides in an inert organic solvent. Copper salts can be used to promote the reaction of aryl halides with alkoxides, and Pd(0) salts can be used to promote the reaction with thioalkoxides.

"Aromatic halogenation" includes the addition of chlorine, bromine or iodine to an aromatic ring optionally with a catalyst, e.g. iron or a Lewis acid. It also includes the reaction of N-chloro and N-bromoamides catalyzed by the addition of acids. For iodination, iodine can be used with copper salts, silver trifluoromethanesulfonate, thallium(I) acetate, or with an oxidizing agent such as nitric acid, iodic acid, sulfur trioxide or hydrogen peroxide. Iodine monochloride can also be used.

"Cross-coupling" includes all cross-coupling methods known by those skilled in the art. Such methods include the reaction of a vinyl or aromatic triflate, bromide or iodide with a tin (Stille-type), zinc, magnesium or boronate (Suzuki-type) derivative catalyzed by a palladium(0), palladium(II), nickel(O) or nickel(II) catalyst. Copper iodide, lithium chloride, zinc chloride or triphenylarsine, tris(2-furyl)phosphine or tris(2,4,6-trimethoxyphenyl) phosphine advantageously can also be added. When a boronic acid derivative is used, the reaction proceeds in the presence of an inorganic base such as potassium phosphate or carbonate or sodium carbonate. The cross-coupling reactions are performed in an inert organic solvent.

"Grignard type reaction" includes the addition of an organometallic compound to a carbonyl-containing compound. This includes addition of Grignard reagents, alkyl or aryllithiums, alkylzinc, alkylaluminum, organotitanium, organozirconium or organocerium compounds in an inert organic solvent such as ethyl ether, THF, DCM, benzene, toluene, or the like. Complexing of the ketone or the Grignard reagent with cerium halides, perchlorate salts or tetraalkylammonium halides can sometimes be advantageous to improve the addition reaction. The term "Grignard type reaction" is also intended to include the addition of a Grignard reagent to an acid chloride that has been first reacted with tributylphosphine to form the corresponding phosphonium salt. The reaction is performed in an inert organic solvent.

"Hydrolysis" includes the hydrolysis of esters and carbonyl protecting groups. For example, methyl or ethyl esters can be removed with aqueous solutions of sodium or potassium alkoxides in THF or EtOH. The hydrolysis of tert-butyl esters advantageously is carried out under acidic conditions such as 90% trifluoroacetic acid or 6N hydrochloric acid in solvents such as THF or DCM. Allyl esters can be removed with Pd(0) catalyst in an organic solvent. Silyl esters such as trimethylsilylethyl esters can be cleaved with tetrabutylammonium fluoride in THF. The hydrolysis of ketals and acetals can be carried out under acidic conditions such as 1 N hydrochloric acid, 80% acetic acid or p-toluenesulfonic acid in solvents such as THF or acetone.

"Imine formation" procedures are known in the field. For example, a ketone can be reacted with an amine in presence of an acid with or without a drying agent. Various inorganic and organic acids can be used, such as zinc chloride, titanium chloride, hydrochloric acid, sulfuric acid, trifluoroacetic acid, acetic acid, p-toluenesulfonic acid and the like, in solvents such as DCM, EtOH, benzene, toluene, THF, DMF and the like.

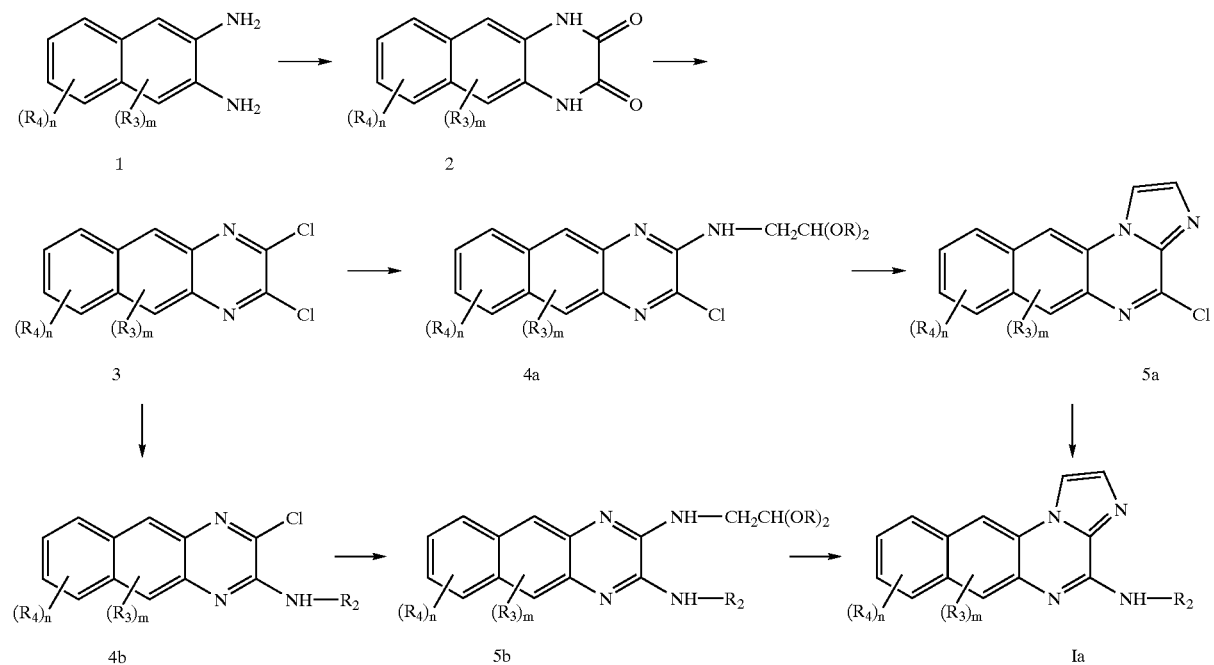

Scheme 1
Benzo-imidazo-quinoxalines

Benzo-imidazo-quinoxalines of formula Ia (wherein $Y_1$ of formula (I) is N, X is $CR_1$ and $R_1$ is hydrogen) can be prepared as above. Substituted 2,3-diaminonaphthalenes 1 are reacted with, for example, diethyl oxalate or oxalyl chloride to give annulated quinoxalinediones 2. Diones 2 are reacted with a chlorinating agent to give dichlorides 3. Dichlorides 3 are reacted with amine reagents comprising aminoacetaldehyde acetal and an appropriate primary amine ($R_2$—$NH_2$), and cyclized, wherein the order of reactivity can be adjusted depending upon chlorine atom reactivity.

For example, dichlorides 3 can first be reacted with an aminoacetaldehyde acetal to give amino-chloro derivatives 4a. The amino-chloro derivatives 4a can be cyclized to give the chloro-benzo-imidazoquinoxaline 5a which can, in turn, be reacted with various primary amines ($R_2$—$NH_2$) to give compounds of formula (Ia).

Alternatively, where the undesired chlorine atom has greater reactivity (e.g., due to substituents R3 and R4), the order of addition of the amine reagents can be reversed, as shown for structures 4b and 5b. Dichloride 3 is reacted with primary amines (R2-NH2) to give amino-chloro derivatives 4b, which are then reacted with an aminoacetaldhyde acetal to give diamino compounds 5b, which are then cyclized to give the compound of formula Ia.

Exemplary aminoacetaldehyde acetals comprise aminoacetaldehyde, dimethyl acetal, or aminoacetaldehyde, diethyl acetal. Cyclization is typically performed under acidic conditions.

Scheme II
1-Substituted benzo-imidazo-quinoxalines

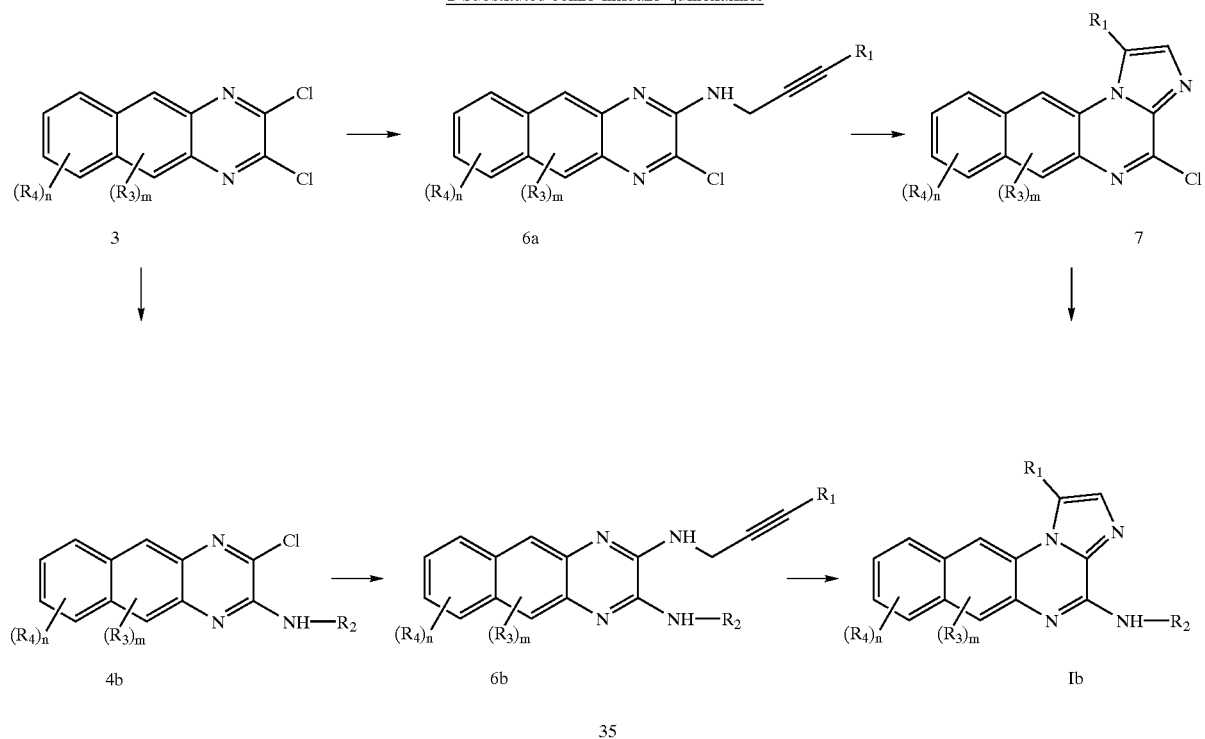

1-Substituted benzo-imidazo(1,2-a)quinoxalines of formula Ib (wherein Y1 of formula (I) is N, X is CR1 and R1 is substituted lower alkyl) can be prepared as shown in Scheme II. Dichloro compounds 3 are prepared as shown in Scheme I and reacted with substituted propargylamines (R1-C≡C—CH2-NH2) to give amino-chloro derivatives 6a, which are cyclized to 1-substituted chloro-benzo-imidazoquinoxalines 7. Suitable primary amines are reacted with 7 to give compounds of formula Ib.

Alternatively, the order of reactivity can be adjusted, wherein dichloro compounds 3 are first reacted with suitable primary amines to give derivatives 4b, as in Scheme I, and then reacted with propargyl amines to amino derivatives 6b, which can be cyclized as above to give compounds of formula Ib.

Scheme III
Benzo-Pyrazolo-Quinazolines

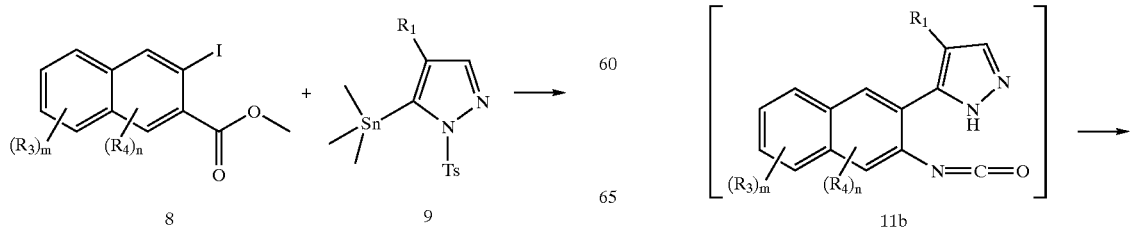

-continued

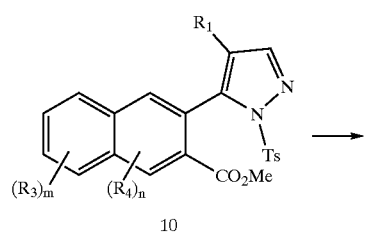

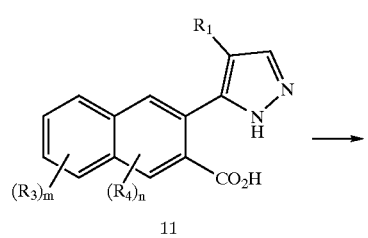

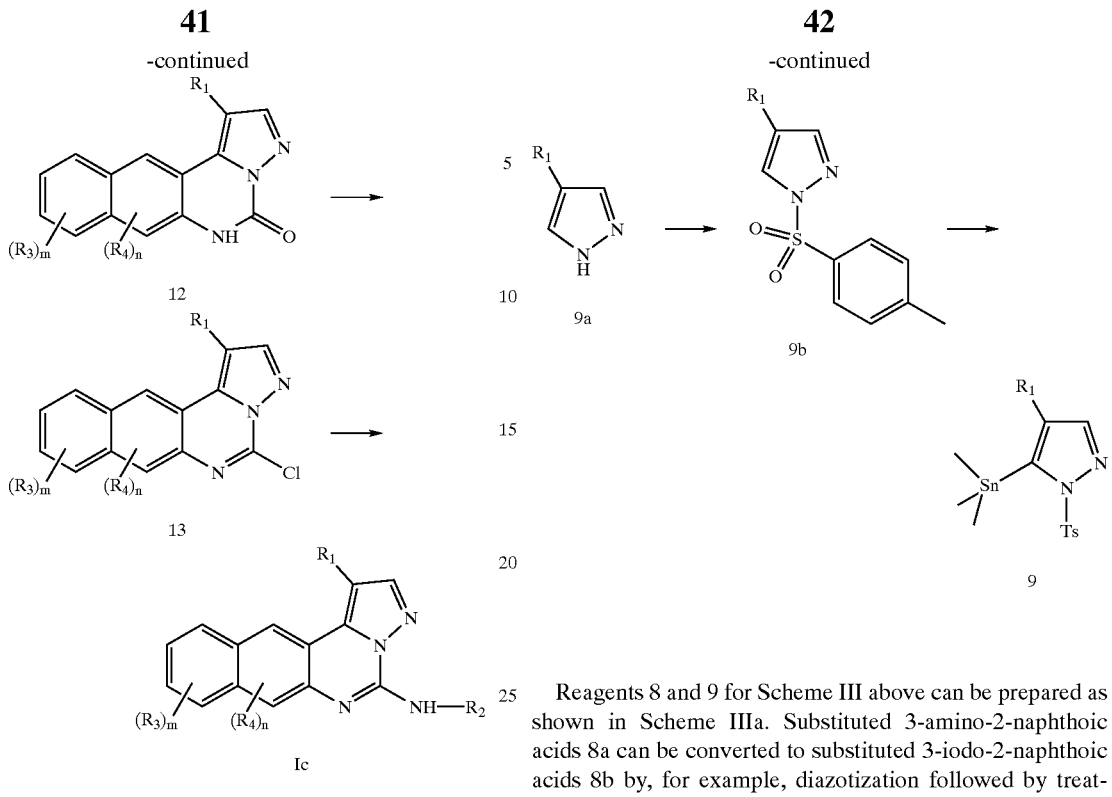

Benzo-pyrazolo-quinazolines of formula Ic (wherein $Y_2$ of formula (I) is N, X is $CHR_1$ and $R_1$ is as defined above) can be prepared as shown in Scheme III. Reagents 8c and 9c are condensed in the presence of catalyst in a Stille-tyoe reaction to give coupled product 10, which is hydrolyzed to give compound 11. Treatment of 11 with, for example, diphenyl phosphoryl azide followed by heat, produces an intermediate isocyanate 11b, which will spontaneously cyclize under the reaction conditions to give compound 12. Treatment of 12 with a chlorinating agent gives chloro compound 13, which can be reacted with suitable primary amines ($R_2$—$NH_2$) to give compounds of formula Ic.

Scheme IIIa

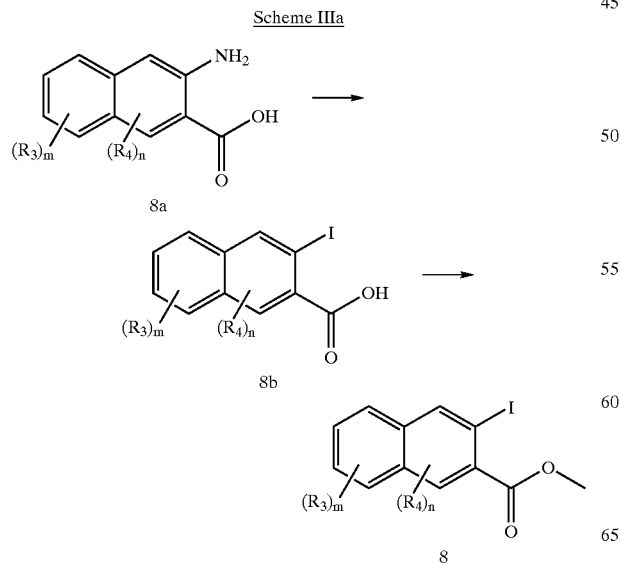

Reagents 8 and 9 for Scheme III above can be prepared as shown in Scheme IIIa. Substituted 3-amino-2-naphthoic acids 8a can be converted to substituted 3-iodo-2-naphthoic acids 8b by, for example, diazotization followed by treatment with an iodide salt. Esterification of compound 8b produces 3-iodo-2-napthoic acid esters 8. 4-Substituted pyrazoles 9a can be treated with a p-toluenesulfonating agent, such as p-toluenesulfonyl chloride, to give p-toluenesulfonamide 9b. Deprotonation of compound 9b with a strong base, such as t-butyl lithium, and treatment with a stannylating agent, such as trimethyl chloro stannane, gives reagent 9.

Scheme IV
Benzo-imidazo-quinolines

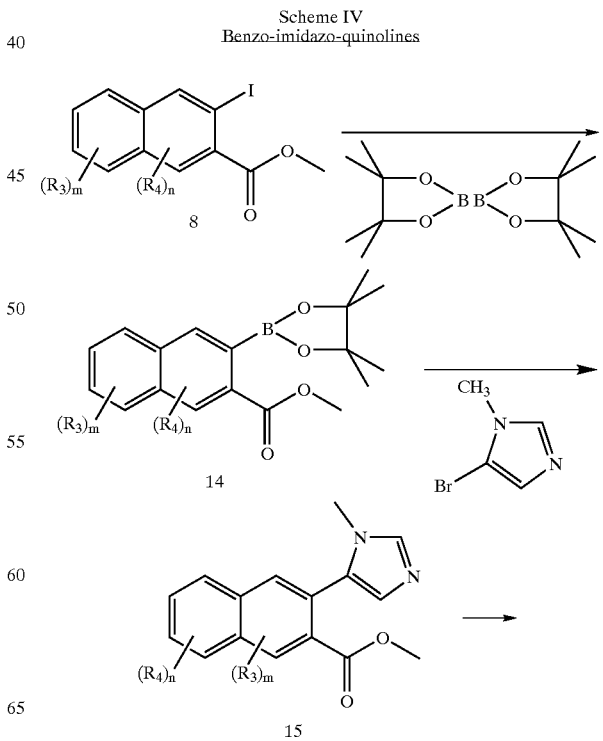

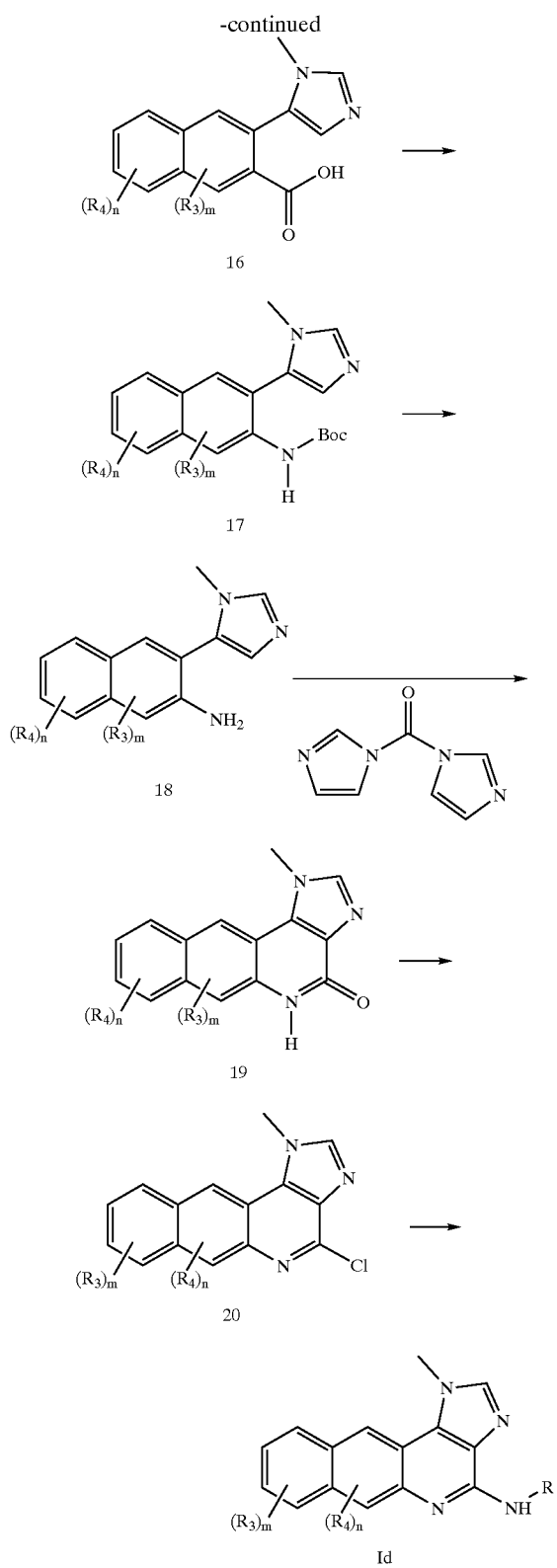

1-methyl-5-bromoimidazole and catalyst in a Suzuki-type reaction gives coupled ester 15. Ester 15 is hydrolyzed to give acid 16, which is converted via treatment with diphenylphosphoryl azide (through an intermediate isocyanate—see 11 b) and t-butanol into protected amine 17. Acid treatment converts 17 to free amine 18, which is heated in a high-boiling point inert solvent such as 1,2-dichlorobenzene with carbonyldiimidazole to give cyclized product 19. Treatment with a chlorinating agent converts compound 19 to the chloro derivative 20, which can be converted by treatment with suitable primary amines ($R_2$—$NH_2$) to give compounds of formula Id.

Scheme V
BENZO(G)THIAZOLO(4,5-C)QUINOLINES

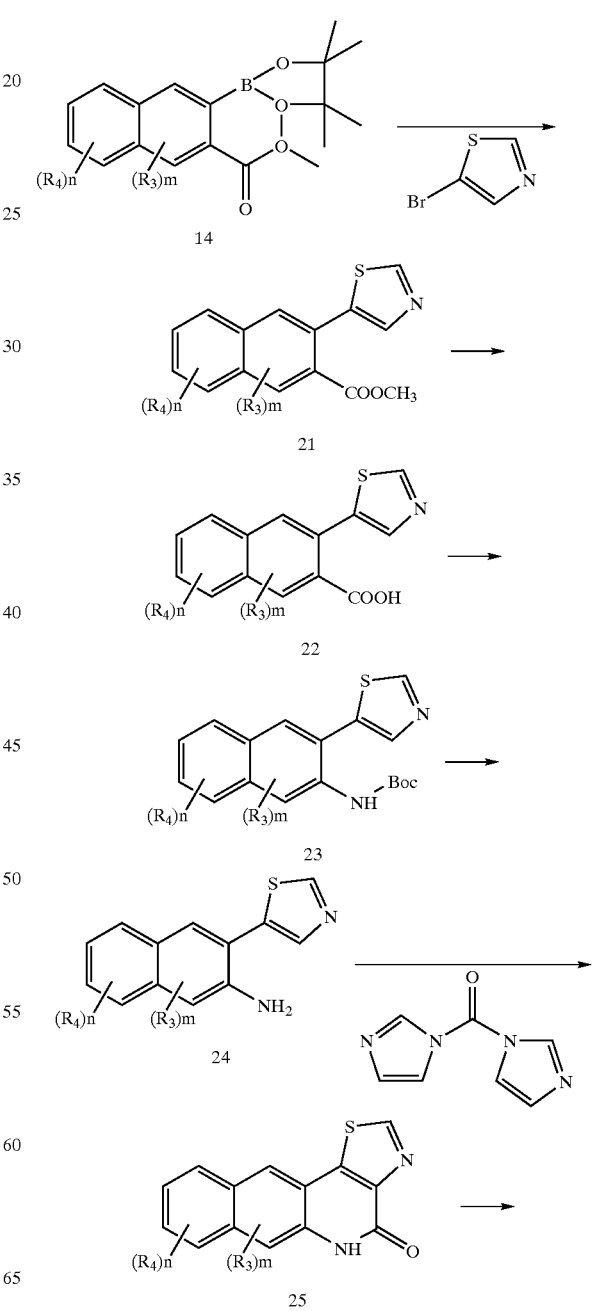

Benzo-imidazo-quinolines of formula Id (wherein X of formula (I) is $NR_1$ and $R_1$ is methyl) can be prepared as shown in Scheme IV. Substituted 3-iodo-2-naphthoic acid esters 8 prepared as in Scheme IIIa are converted to boronate derivatives 14 using catalyst and a reagent such as bis(pinacolato)diboron. Condensation of compound 14 with -continued

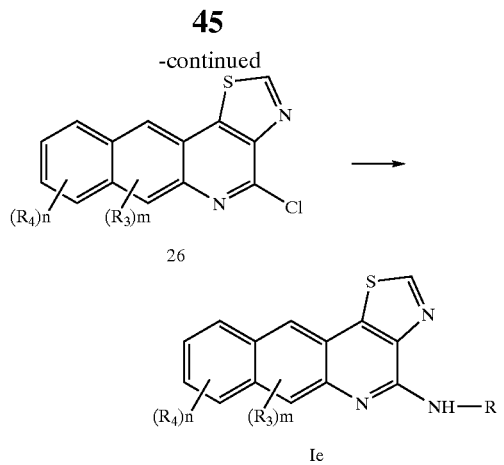

Benzo-thiazolo-quinolines can be prepared as shown above in Scheme V. Substituted 3-boronato-2-naphthoic acid ester 14 is condensed with 5-bromothiazole in a Suzuki-type reaction, catalyzed by a metal such as Pd, to give coupled product 21. The ester 21 is hydrolyzed under standard conditions to give acid 22, which is then converted via treatment with diphenylphosphoryl azide (through an intermediate isocyanate similar to 11 b) and t-butanol into the protected amine 23. Acid treatment can convert compound 23 to the free amine 24, which is heated in a high-boiling inert solvent such as 1,2-dichlorobenzene with carbonyldiimidazole to give cyclized product 25. Compound 25 can be converted to the chloro derivative 26 by treatment with a chlorinating agent, and compound 26 is converted by treatment with suitable primary amines ($R_2$—$NH_2$) to give the compound of formula Ie.

The following preparations illustrate embodiments of the invention and are not intended to limit the scope of the claims. The reagents and starting materials of Preparations 1–19 are useful in synthesizing compounds of formula (I), or salts thereof, such as illustrated in Schemes I–V. In the following preparations, anhydrous reactions were performed under an atmosphere of nitrogen or argon using either commercially available dry solvents or freshly distilled solvents. Melting points were determined in an open capillary tube with a Thomas-Hoover melting point apparatus. Column chromatography was performed using EM Science silica gel 60 (230–400 mesh) with the designated solvent system as eluant. Thin-layer chromatography was done on E. Merck silica gel 60 $F_{254}$ plates (0.5 mm). HPLC purity determinations were done using either an HP 1090 DR5 with a diode array detector and a Waters Nova-Pak C18 column (3.9×150 mm), or a Shimadzu LC-10AS with a SPD-10AV UV-Vis detector and one of the following columns: YMC Combiscreen ODS—A (4.6×50 mm); HP Zorbax SB-C18 (4.6×750 mm). Infrared spectra and $^1$HNMR spectra were recorded and chemical shifts are expressed in parts per million (ppm or δ) with the solvent in use as internal standard. Coupling constants are given in Hertz and multiplets are designated as follows; singlet (s), doublet (d), triplet (t), quartet (q), muliplet (m), and broad (br). Low resolution mass spectra were determined on a Finnigan Matt TSQ-7000 triple stage quadrapole spectrometer (positive/negative ESI) operated in the negative ion mode.

Preparation of Reagents and Starting Materials for the Preparation of Compounds of Formula (I)

Preparation 1

1,4-Dihydrobenzo[g]quinoxalin-2,3-dione

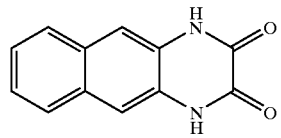

A mixture of 2,3-diaminonaphthalene (2.87 g, 18.14 mmol) and diethyl oxalate (30 mL, 223 mmol) was heated to reflux for 14 hours, cooled to RT and filtered. The residue was washed with EtOH and dried in vacuo to give the title compound as a brown solid (3.15 g, 82%); mp>350° C.; IR (KBr, cm$^{-1}$) 3045, 2942, 2869,1716, 1642,1406, 877; $^1$H NMR (DMSO) δ 12.11 (s, 2H), 7.84–7.81 (m, 2H), 7.54 (s, 2H) 7.39 (dd, J=6.3, 3.0, 2H); LC/MS 92.5% (220 nm), m/z (M+H$^+$) 213.

Preparation 2

2,3-Dichlorobenzo[g]quinoxaline

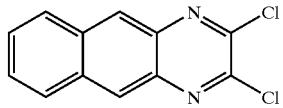

One gram (1 g; 4.72 mmol) of 1,4-dihydrobenzo[g]quinoxalin-2,3-dione was stirred in 2 ml of phosphorus oxychloride for 5 hours at reflux. The mixture was concentrated by evaporation and dried under high vacuum. A saturated $K_2CO_3$ solution was carefully added to the residue, and the solid was filtered off and washed with water to afford the title compound as a brown solid (1.00 g, 85%); mp 239–242° C.; IR (KBr, cm$^{-1}$) 1200, 1109, 998, 886, 748; $^1$H NMR (DMSO) δ 8.78 (s, 2H), 8.31–8.28 (m, 2H), 7.75–7.73 (m, 2H).

Preparation 3

2-chloro-3-(propargylamino)benzo[g]quinoxaline

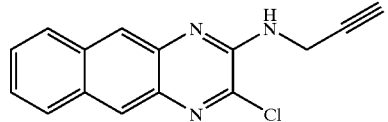

A mixture of 2,3-dichlorobenzo[g]quinoxaline (0.634 g, 2.55 mmol), propargylamine (0.21 ml, 3.05 mmol) and TEA (0.53 mL, 3.83 mmol) in 15 mL of dioxane was heated to reflux for 4.5 hours. After evaporating the resulting mixture under vacuum, the crude product was chromatographed (CH$_2$Cl$_2$) to afford the title compound as a yellow solid (0.496 g, 73%); mp 169–172° C.; IR (KBr, cm$^{-1}$) 3412, 3283, 3235, 1570, 1508, 1335; $^1$H NMR (DMSO) δ 8.44 (s, 1H), 8.26 (s, 1H), 8.16–8.06 (m, 3H), 7.58–7.54 (m, 1H), 7.51–7.48 (m, 1H), 4.28 (dd, J=6.1, 2.5, 2H), 3.12 (t, J=2.5, 1H); LC/MS 97.8% (220 nm), m/z (M+H$^+$) 268.

Preparation 4

4-chloro-1-methylbenzo[g]imidazo[1,2-a]quinoxaline

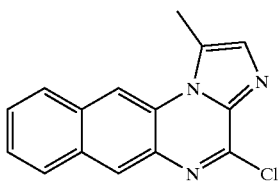

2-Chloro-3-(propargylamino)benzo[g]quinoxaline (0.420 g, 1.57 mmol) was treated with 4 mL of concentrated $H_2SO_4$ and the mixture was stirred at 80° C. for 1 hour, cooled to RT and poured into ice water. The mixture was cautiously neutralized with aqueous NaOH, and the resulting precipitate was filtered, washed with water, and dried in vacuo to give the title compound as a beige solid (0.124 g, 30%); mp 221–223° C.; IR (KBr, cm$^{-1}$)1538, 1479, 1456, 1398, 1101, 919; $^1$H NMR (DMSO) δ 8.79 (s, 1H), 8.53 (s, 1H), 8.23 (d, J=8.1, 1H), 8.13 (d, J=8.5, 1H), 7.69–7.59 (m, 3H), 3.04 (s, 3H); LC/MS 100% (220 nm), m/z (M+H$^+$) 268.

Preparation 5

3-Iodo-2-napthoic Acid

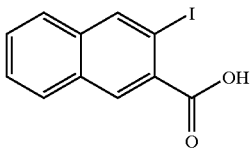

To a beaker of 3-amino-2-napthoic acid (6.01 g, 80% pure; 25.69 mmol), was added a solution of concentrated HCl (10.0 mL) and water (15.0 mL). After the resulting pink paste was stirred for 17 min, it was cooled to 0° C. and treated with a solution of water (10 mL) and $NaNO_2$ (2.54 g, 36.81 mmol) drop-wise (over 8 min). One minute later, the brown reaction mixture was treated with a cooled (0° C.) water (10.0 mL) solution of KI (10.0 g, 60.24 mmol) drop-wise (over 12 min). The cooling bath was removed, water (15 mL) was added, and the reaction mixture was stirred for 10 min at RT and heated at 95° C. for 65 min. It was then diluted with water (50 mL) and extracted with EtOAc (250 mL). The organic layer was washed with water (50 mL) and brine, dried (MgSO$_4$), filtered, and evaporated in vacuo. The resultant crude material was submitted to flash chromatography (sample was loaded as a silica gel mesh; EtOAc) to afford the title compound as an iodine colored fluffy solid weighing ~6.50 g. $^1$H NMR (DMSO, δ=2.50): 13.36 (br s, 1H), 8.63 (s, 1H), 8.37 (s, 1H), 8.05 (d, J=7.9, 1H), 7.93 (d, J=8.0, 1H), 7.67–7.60 (m, 2H).

Preparation 6

Methyl 3-Iodo-2-napthoate

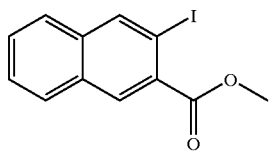

To 3-iodo-2-napthoic acid (Preparation 5) (6.50 g), were added MeOH (100 mL) and concentrated $H_2SO_4$ (2 mL), and the resultant heterogeneous mixture was refluxed for 13 hr. The reaction mixture was allowed to cool to RT, then neutralized with NaHCO$_3$ (6.0 g), and the volatile component was removed in vacuo. The residue was partitioned between water (50 mL) and EtOAc (300 mL). The organic layer was washed with $Na_2S_2O_3$ solution (4.2 g +50 mL of water) and brine, dried (MgSO$_4$), filtered and evaporated in vacuo. The resulting crude material was submitted to flash chromatography (sample was loaded as a silica gel mesh, 10% EtOAc/hexanes) to isolate the title compound as a light-yellow solid (5.50 g, 2 steps combined yield of 69%). $^1$H NMR (DMSO, δ=2.50): 8.66 (s, 1H), 8.39 (s, 1H), 8.06 (d, J=8.0, 1H), 7.95 (d, J=8.0, 1H), 7.69–7.62 (m, 2H), 3.91 (s, 3H). (DCI) m/z (M+H)$^+$=313.0. Anal. calculated for $C_{12}H_9IO_2$: C, 46.18; H, 2.91. Found: C, 46.28; H, 2.85.

Preparation 7

4-Methyl-1-(4-tolunesulfonyl)pyrazole

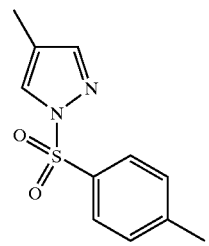

p-TsCl (9.81 g, 51.46 mmol) was added in batches over a few minutes to a $CH_2Cl_2$ (100 mL) solution of 4-methylpyrazole (4.00 g, 48.72 mmol) and pyridine (6.0 mL, 74.18 mmol). The reaction mixture was stirred for 95 min, then diluted with $CH_2Cl_2$ (250 mL) and washed with NaHCO$_3$ solution [a mixture of sat'd NaHCO$_3$ solution (20 mL) and $H_2O$ (40 mL)], and water (60 mL). The organic layer was dried (MgSO$_4$), filtered and evaporated in vacuo. The resulting crude material was purified by flash chromatography (sample was loaded as a silica gel mesh; $CH_2Cl_2$) to afford the title compound as a white solid (10.88 g, 95%). $^1$H NMR (CDCl$_3$, δ=7.26): 7.87 (d, J=8.4, 2H), 7.84 (s, 1H), 7.54 (s, 1H), 7.32 (d, J=8.40, 2H), 2.41 (s, 3H), 2.06 (s, 3H). (ESI) m/z (M+H)$^+$=236.7. Anal. calculated for $C_{11}H_{12}N_2O_2S$: C, 55.91; H, 5.12; N, 11.86. Found: C, 55.81; H, 4.94; N, 11.76.

Preparation 8

4-Methyl-1-(4-tolunesulfonyl)-5-trimethylstannylpyrazole

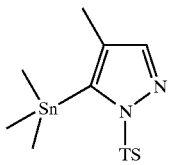

t-BuLi (1.7 M/pentane) was added over 10 min to a cooled (−78° C.) THF (60 mL) semi-suspension of 4-methyl-1-(4-tolunesulfonyl)pyrazole (Preparation 7) (6.01 g, 25.43 mmol). After the mixture was stirred for 10 min, it was treated drop-wise (over 20 min) with Me$_3$SnCl (28.0 mL of 1.0 M/THF, 28.0 mmol). The resulting mixture was stirred for 4.3 hr while the bath was allowed to thaw to −55° C., and then for 70 min. at RT. The reaction mixture was diluted with EtOAc (250 mL) and washed with water (50 mL) and brine, dried (MgSO$_4$), filtered, and evaporated in vacuo. The crude material was submitted to flash chromatography (sample was loaded as a silica gel mesh; 15–20% EtOAc/hexanes) to afford the title compound as a dense white solid (4.406 g, 43%). Non-consumed pyrazole of Preparation 7, above, was also retrieved (1.954 g, 33%). $^1$H NMR of the title compound (DMSO, δ=2.50): 7.74 (s, 1H), 7.70 (d, J=8.3, 2H), 7.45 (d, J=8.3, 2H), 2.38 (s, 3H), 2.08 (s, 3H; satellite peaks due to Sn-H with J=4.5), 0.45 (s, 9H; satellite peaks due to Sn-H with J=59.8 and 57.3). (ESI) m/z (M+H)$^+$=400.9.

Preparation 9

Methyl 3-(4-methyl-1-(4-toluenesulfonyl)pyrazol-5-yl)-2-naphthoate

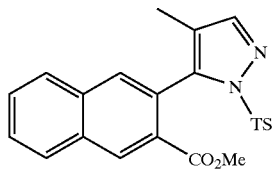

DMF (26.0 mL) was added into a mixture of methyl-3-iodo-2-napthoate (Preparation 6) (2.017 g, 6.463 mmol), 4-methyl-1-(4-tolunesulfonyl)-5-trimethylstannylpyrazole (Preparation 8) (2.895 g, 7.254 mmol), Pd$_2$ dba$_3$ (236 mg, 0.258 mmol), Ph$_3$As (317.2 mg, 1.036 mmol), and CuI (130.7 mg, 0.686 mmol). After nitrogen was bubbled through the heterogeneous mixture for a few minutes, it was stirred at RT for 7 min and at 90° C. for 12 hr. The volatile component was removed in vacuo, and the resultant viscous residue was submitted to flash chromatography (sample was loaded as a silica gel mesh; 0–10% EtOAc/CH$_2$Cl$_2$) to afford the titled compound as a yellow solid (1.485 g, 55%). $^1$H NMR (DMSO, δ=2.50): 8.73 (s, 1H), 8.23 (d, J=7.7, 1H), 8.05 (d, J=7.7, 1H), 7.83 (s, 1H), 7.81 (s, 1H), 7.77–7.71 (m, 2H), 7.50 (d, J=8.2, 2H), 7.38 (d, J=8.2, 2H), 3.66 (s, 3H), 2.38 (s, 3H), 1.77 (s, 3H). (ESI) m/z (M+H)$^+$=421.0.

Preparation 10

3-(4-methylpyrazol-5-yl)-2-naphthoic Acid

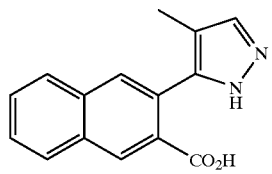

THF (12.0 mL), MeOH (8.0 mL) and NaOH solution (7.5 mL of 1.0 N/H$_2$O) were added to methyl-3-(4-methyl-1-(4-tolunesulfonyl)pyrazol-5-yl)-2-napthoate (Preparation 9) (1.240 g, 2.949 mmol), and the reaction mixture was heated at 80° C. for 4.2 hr. It was then diluted with water (20 mL), acidified to pH ~4.5 with 1 N HCl, and extracted with EtOAc (75 ml, 2×). The combined organic layer was washed with brine, dried (MgSO$_4$), filtered, and evaporated in vacuo. The resulting crude material was submitted to flash chromatography (sample was loaded as a silica gel mesh; 10% MeOH/CH$_2$Cl$_2$) to isolate the title compound as faint-yellow solid (300 mg, 40%). $^1$H NMR (DMSO, δ=2.50; one tautomer was observed): 12.70 (br s, 2H), 8.37 (s, 1H), 8.08 (d, J=7.9, 1H), 8.01 (d, J=8.0, 1H), 7.93 (s, 1H), 7.65–7.58 (m, 2H), 7.47 (s, 1H), 2.01 (s, 3H). (ESI) m/z (M+H)$^+$=252.99.

Preparation 11

1-Methylbenzo(g)pyrazolo 1,5-c)quinazolin-5-one

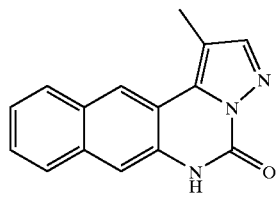

Et$_3$N (300 μL, 2.152 mmol) and (PhO)$_2$PON$_3$ (440 μL, 2.064 mmol) were added to a C$_6$H$_6$ (10.0 mL) suspension of 3-(4-methylpyrazol-5-yl)-2-naphthoic acid (Preparation 10) (257 mg, 1.019 mmol), and the mixture was heated at 50° C. for 2 hr. The volatile component was removed in vacuo, and the resulting yellow solid was dissolved in o-dichlorobenzene (8.0 mL) and heated at 150° C. for 4 hr. During the latter heating, there was a gradual evolution of gas accompanied by the formation of a suspension. The reaction mixture was allowed to cool to RT, and the precipitate was filtered and washed with copious ether to afford the title compound as a fluffy light-yellow solid (170.8 mg, 67%). $^1$H NMR (DMSO, δ=2.50): 11.86 (s, 1H), 8.57 (s, 1H), 8.13 (d, J=8.2, 1H), 7.99 (s, 1H), 7.92 (d, J=8.3, 1H), 7.22 (s, 1H), 7.56 (app t, J=7.21, 1H), 7.49 (app t, J=7.48, 1H), 2.60 (s, 3H). (ESI) m/z (M+H)$^+$=250.00.

Preparation 12

1-Methyl-5-chlorobenzo(g)pyrazolo(1,5-c)quinazoline

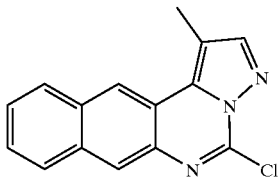

PhNEt$_2$ (1.50 mL) and POCl$_3$ (15.0 mL) were added to 1-methylbenzo(g)pyrazolo(1,5-c)quinazolin-5-one (Preparation 11) (184.7 mg, 0.741 mmol), and the resulting heterogeneous mixture was heated at reflux for 46 hr. During heating, the suspension (the starting material), gradually started to dissolve. The dark-green reaction mixture was filtered to remove non-consumed starting material (16.2 mg, 8.8%), and the filtrate was exposed to high vacuum to remove most of the POCl$_3$. The residue was partitioned between water (30 mL) and EtOAc (70 mL). The organic layer was washed with brine, dried (MgSO$_4$), filtered, and evaporated in vacuo. The crude material was submitted to flash chromatography (sample was loaded as a silica gel mesh; 20% EtOAc/hexanes) to afford the title chloride as an off-white solid (153 mg, 77%). $^1$H NMR (DMSO, δ=2.50): 8.80 (s, 1H), 8.46 (s, 1H), 8.29–8.27 (m, 1H), 8.19 (s, 1H), 8.17–8.15 (m, 1H), 7.70–7.65 (m, 2H), 2.70 (s, 3H). (ESI) m/z (M+H)$^+$=267.98.

Preparation 13

Methyl-3-(4,4,5,5-tetramethyl-1,3,2-dioxaborolan-2-yl)-2-naphthoate

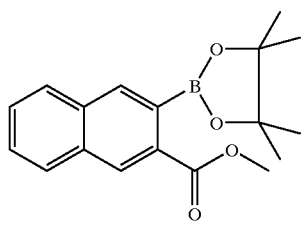

To a solution of 4,4,4',4',5,5,5',5'-octamethyl-2,2'-bi-1,3,2-dioxaborolane (30.0 g, 0.118 mol) and methyl 3-iodo-2-naphthoate (Preparation 6) (33.5 g, 0.107 mol) in DMSO (600 mL) were added PdCl$_2$(dppf) (2.62 g, 0.21 mmol) and KOAc (31.51 g, 0.321 mol). The mixture was degassed and purged with N$_2$, and then heated at 85° C. for 18 hours. The brown reaction mixture was cooled to RT, diluted with water (1.5 L), and extracted with EtOAc (2.5 L, then 2×500 mL). The combined organic layer was washed with brine (9×500 mL), dried over MgSO$_4$, filtered and evaporated in vacuo. The resulting crude material was submitted to flash chromatography (2.0% MeOH/CHCl$_3$), affording the title compound as a yellow solid (19.5 g, 58%). $^1$H NMR (CDCl$_3$): 8.50 (s, 1H), 7.99 (s, 1H), 7.90 (d, J=8.1, 1H), 7.86 (d, J=8.1, 1H), 7.57 (m, 1H), 7.54 (m, 1H), 3.98 (s, 3H), 1.47 (s, 12H). (ESI) m/z (M+H)$^+$=313.16

Preparation 14

Methyl-3-(1-methyl-imidazol-5-yl)-2-naphthoate

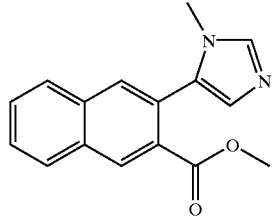

To a mixture of methyl-3-(4,4,5,5,-tetramethyl-1,3,2-dioxaborolan-2-yl)-2-naphthoate (Preparation 13) (15.37 g, 49.3 mmol) and 5-bromo-1-methyl-1H-imidazole (9.06 g, 49.3 mmol) in toluene/EtOH (350 mL/36 mL) were added Pd(PPh$_3$)$_4$ (11.37 g, 9.84 mmol), Na$_2$CO$_3$ (20.9 g, 197.2 mmol) and water (106 mL). The mixture was degassed, purged with N$_2$, and heated to reflux for 20 hours. It was then cooled to RT, neutralized with HCl (1.0 N, 100 mL), and concentrated in vacuo. The residue was partitioned between water (300 mL) and EtOAc (1 L). The organic layer was washed with water (2 L) and brine, dried over MgSO$_4$, filtered and evaporated in vacuo. The resulting crude material was submitted to flash chromatography (1.5% MeOH/CHCl$_3$), furnishing the title compound as a light-yellow solid (9.5 g, 72%). $^1$H NMR (CDCl$_3$): 8.53 (s, 1H), 7.99 (d, J=8.1, 1H), 7.80 (d, J=8.1, 1H), 7.77 (s, 1H), 7.56 (m, 1H), 7.54 (m, 1H), 7.54 (s, 1H), 6.94 (s, 1H), 3.73 (s, 3H), 3.29 (s, 3H). (ESI) m/z (M+H)$^+$=267.11.

Preparation 15

3-(1-Methyl-imidazol-5-yl)-2-naphthoic Acid

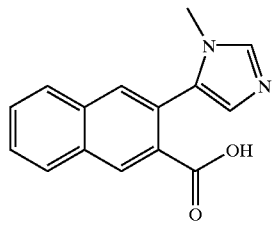

A solution of methyl-3-(1-methyl-imidazol-5-yl)-2-naphthoate (Preparation 14) (8.5 g, 32 mmol) in THF/MeOH (3/2,120 mL) was treated with aqueous NaOH (1.0 N, 48 mL). After 20 hours at RT, it was neutralized with aqueous HCl (1.0 N, 20 mL). The solvent was evaporated in vacuo. The solid residue was treated with MeOH (5 mL), then evaporated again. The resulting crude material was purified by flash chromatography (5% MeOH/EtOAc) affording the title compound as a pale-yellow solid (6.0 g, 74%). $^1$H NMR (CDCl$_3$): 8.34 (s, 1H), 7.95 (d, J=8.1, 1H), 7.90 (d, J=8.1, 1H), 7.72 (s, 1H), 7.53 (s, 1H), 7.52 (m, 1H), 7.50 (m, 1H), 6.83 (s, 1H), 3.16 (s, 3H). (ESI) m/z (M+H)$^+$=253.10.

Preparation 16

1,1-Dimethylethyl-3-((1-methylimidazol-5-yl)-2-naphthyl)carbamate

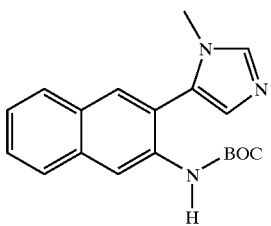

To a mixture of 3-(1-methyl-imidazol-5-yl)-2-naphthoic acid (Preparation 15) (1.0 g, 3.95 mmol) and Et$_3$N (1.1 mL, 7.91 mmol) in 20 ml t-BuOH was added diphenylphosphorylazide (1.63 g, 5.93 mmol). After 40 minutes at 80° C., the mixture was cooled to RT. The slurry was diluted with EtOAc (300 mL), and washed once with water (50 mL) and three times with brine. The organic layer was dried over MgSO$_4$, filtered, and evaporated in vacuo. The crude material was submitted to flash chromatography (0.5% MeOH/EtOAc) affording the title compound as a pale-yellow solid (0.67 g, 51%). $^1$H NMR (CDCl$_3$): 8.34 (s, 1H), 7.95 (d, J=8.1, 1H), 7.90 (d, J=8.1, 1H), 7.72 (s, 1H), 7.53 (s, 1H), 7.52 (m, 1H), 7.50 (m, 1H), 6.83 (s, 1H), 3.16 (s, 3H), 1.43 (s, 9H). (ESI) m/z (M+H)$^+$=324.15

Preparation 17

5-(3-Amino-2-naphthyl)-1-methylimidazole

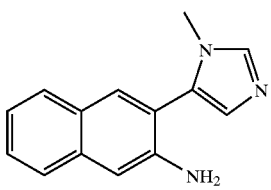

A solution of 1,1-dimethylethyl-3-((1-methylimidazol-5-yl)-2-naphthyl)carbamate (Preparation 16) (1.0 g, 2.98 mmol) in TFA/CH$_2$Cl$_2$ (1:10, 50 mL) was stirred at RT for 18 hours. After concentration, the residue was diluted with EtOAc (200 mL), washed with aqueous NaHCO$_3$ (100 mL) and brine. The organic layer was then dried over MgSO$_4$, filtered and evaporated in vacuo. The crude material was submitted to flash chromatography (5% MeOH/EtOAc) affording the title compound as a light yellow solid (0.49 g, 70%). $^1$H NMR (CDCl3): 7.65 (d, J=8.1, 1H), 7.59 (d, J=8.1, 1H), 7.57 (s, 1H), 56 (s, 1H), 7.36 (m, 1H), 7.22 (m, 1H), 7.13 (s, 1H), 7.03 (s, 1H), 3.96 (b, 2H), 3.46 (s, 3H). (ESI) m/z (M+H)$^+$=224.08

Preparation 18

1-methyl-4,5-dihydrobenzo(g)imidazo(4,5-c)quinolin-4-one

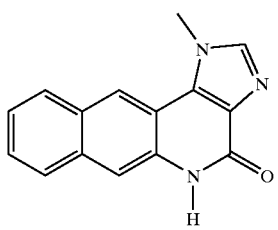

A mixture of 5-(3-amino-2-naphthyl)-1-methylimidazole (Preparation 17) (0.48 g, 2.14 mmol) and 1,1'-carbonyldiimidazole (0.42 g, 2.57 mmol) in o-dichlorobenzene (22 mL) was heated at 180° C. for 5 hours. The suspension was cooled to RT, filtered, and dried under vacuum, affording the title compound as a light yellow solid (0.22 g, 42%). $^1$H NMR (DMSO): 11.57 (s, 1H), 8.71 (s, 1H), 8.15 (s, 1H), 8.10 (d, J=8.4, 1H), 7.89 (d, J=8.4, 1H), 7.84 (s, 1H), 7.53 (m, 1H), 7.46 (m, 1H), 4.30 (s, 3H). (ES m/z (M+H)$^+$=250.08.

Preparation 19

1-Methyl-4-chlorobenzo(q)imidazo(4,5-c)quinoline

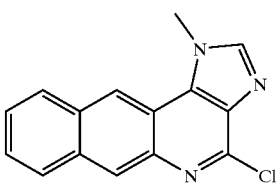

To a mixture of 1-methyl-4,5-dihydrobenzo(g)imidazo(4,5-c)quinolin-4-one (Preparation 18) (200 mg, 0.80 mmol) and PhNEt$_2$ (2.5 mL, 1.6 mmol) was added POCl$_3$ (8 mL). The mixture was then heated to reflux for 4 hours. After cooling, excess POCl$_3$ was removed under vacuum. The residue was diluted with EtOAc (150 mL), and treated with NaHCO$_3$ (1 g) to neutralize the acid. The organic layer was washed with brine, dried over MgSO$_4$, filtered and evaporated in vacuo. The crude material was submitted to flash chromatography (EtOAc) affording the title compound as a light yellow solid (0.18 g, 90%). $^1$H NM R(CDCl$_3$): 8.61 (s, 1H), 8.57 (s, 1H), 8.01 (d, J=8.8, 1H), 7.98 (d, J=8.8, 1H), 7.89 (s, 1H), 7.57 (m, 1H), 7.54 (m, 1H), 4.35 (s, 3H). (ESI) m/z (M+H)$^+$=268.08.

Examples 12–19 provide compounds as described herein.

Example 12

1-methyl-4-methylaminobenzo[g]imidazo[1,2-a]quinoxaline

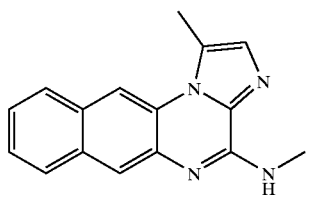

To a solution of 4-chloro-1-methylbenzo[g]imidazo[1,2-a]quinoxaline (0.063 g, 0.236 mmol) (Preparation 4 in Example 11) in of THF was added MeNH$_2$ (40% in H$_2$O, 0.16 mL, 1.88 mmol). The reaction tube was sealed and the mixture stirred at 80° C. for 18 hours. The cooled mixture was then taken up in EtOAc, washed with water and brine, dried (Na$_2$SO$_4$) and evaporated. The resulting residue was recrystallized using i-PrOH to give Example 12 as beige needles (0.043 g, 69%); mp 201–202° C., IR (KBr, cm$^{-1}$) 3324, 1575, 1557, 1411, 1121; $^1$H NMR (DMSO) δ 8.62 (s, 1H), 8.10 (s, 1H), 8.08 (d, J=8.1, 1H), 7.94 (d, J=8.1, 1H), 7.77 (br d, J=4.5, 1H), 7.49–7.45 (m, 2H), 7.35 (s, 1H), 3.06 (d, J=4.6, 3H), 2.98 (s, 3H); MS ($^+$ESI, M+H$^+$) m/z 263; HPLC: 99.5% (230 nm); HRMS calculated for C$_{16}$H$_{14}$N$_4$: 262.1219; found 262.1226. Inhibition of IKK-1 activity was measured using the assay of Example 2, where the inhibitory potential of the compound of Example 12 resulted in an IC$_{50}$ of 0.23 μM.

Example 13

1-methyl-4-(2-N-methylaminoethylamino)benzo[g]imidazo[1,2-a]quinoxaline Hydrochloride

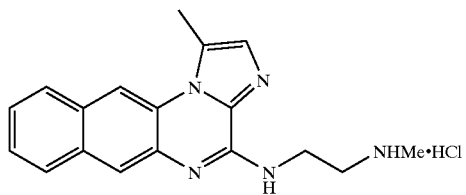

To a solution of 4-chloro-1-methylbenzo[g]imidazo[1,2-a]quinoxaline (0.075 g, 0.281 mmol) (Preparation 4 in Example 11) in 4 mL of THF was added N-methylethylene diamine (0.20 mL, 2.25 mmol). The reaction tube was sealed and the mixture stirred at 80° C. for 18 hours. The resulting cooled mixture was then taken up in EtOAc, washed with water and brine, dried (Na$_2$SO$_4$) and evaporated. Purifying the residue by preparative TLC(CH$_2$Cl$_2$:MeOH, 8:2) yielded 1-methyl-4-(2-N-methylaminoethylamino)benzo[g]imidazo[1,2-a] quinoxaline. This solid was dissolved in CH$_2$Cl$_2$/EtOH and a solution of 1 N HCl in EtOH was added to form the hydrochloride salt, which was filtered, washed with EtOH and dried in vacuo to afford the above titled salt as an off-white solid (0.025 g, 26%); mp 265–275° C. dec; IR (KBr, cm$^{-1}$) 3448, 2958, 2780, 1656, 1532, 1420; $^1$H NMR (CD$_3$OD) 8.72 (s, 1H), 8.42 (s, 1H), 8.13–8.11 (m, 1H), 8.01–7.98 (m, 1H), 7.63–7.57 (m, 3H), 4.23–4.20 (m, 2H), 3.54–3.51 (m, 2H), 3.07 (s, 3H), 2.86 (s, 3H); MS ($^+$ESI, M+H$^+$) m/z 306; HPLC: 98.3% (230 nm); HRMS calculated for C$_{18}$H$_{19}$N$_5$: 306.1719; found 306.1708. Inhibition of IKK-1 activity was measured using the assay of Example 2, where the inhibitory potential of the compound of Example 13 resulted in an IC$_{50}$ of 0.35 μM.

Example 14

1-methyl-4-methylaminobenzo[g]pyrazolo[1,5-c]quinazoline

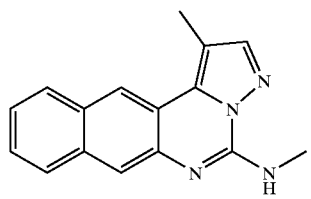

A mixture of 4-methyl-1-(4-tolunesulfonyl)-5-trimethylstannylpyrazole (Preparation 8 in Example 11) (24.0 mg, 0.0896 mmol) and MeNH$_2$ (3.0 mL of 2.0 M/THF, 6.0 mmol) in a pressure tube was heated at 60° C. for 5 hr. After the reaction mixture was cooled to RT, it was treated with NaHCO3 (57 mg) and water (2 pipet-drops) and stirred for 5 min. Silica gel was added and the volatile component was removed in vacuo. The resulting silica gel mesh was submitted to flash chromatography (20% EtOAc/hexanes) to afford the title compound as a light yellow solid (23.0 mg, 98%). $^1$H NMR (DMSO, δ=2.50): 8.60 (s, 1H), 8.10 (s, d, J=8.3, 1H), 8.03 (s, 1H), 8.01 (s, 1H), 7.95 (d, J=8.01, 1H), 7.92 (q, J=4.7, 1H), 7.50 (t, J=7.5, 1H), 7.44 (t, J=7.4, 1H), 3.09 (d, J=4.7, 3H), 2.66 (s, 3H). (ESI) m/z (M+H)$^+$=263.02. Inhibition of IKK-1 activity was measured using the assay of Example 2, where the inhibitory potential of the compound of Example 14 resulted in an IC$_{50}$ of 0.67 μM.

Example 15

1-methyl-4-(2-N-methylaminoethylamino)benzo[g]pyrazolo[1,5-c]quinazoline

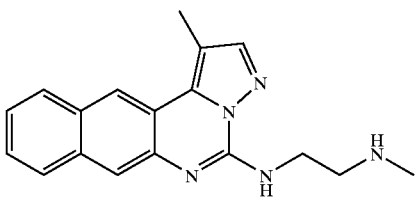

N-methyl-ethylenediamine (250 μL, 2.836 mmol) was added rapidly to a THF (2.0 mL) semi-suspension of 4-methyl-1-(4-tolunesulfonyl)-5-trimethylstannylpyrazole (Preparation 8 in Example 11) (30.5 mg, 0.114 mmol). The reaction mixture was stirred at RT for 1 hr and at 75° C. for 2.3 hr. After the reaction mixture was cooled to RT, it was treated with NaHCO$_3$ (57 mg) and water (2 pipet-drops) and stirred for a few minutes. The volatile components, including the excess diamine, were removed in vacuo. The crude material was submitted to flash chromatography (sample was loaded as a silica gel mesh; 0–100% MeOH/EtOAc) to afford the title compound as a yellow waxy-solid (43.4 mg; the weight is 8.6 mg more than the theoretical yield). $^1$H NMR (DMSO, δ=2.50): 8.60 (s, 1H), 8.10 (d, J=8.1, 1H), 8.02 (s, 2H, signal overlap), 7.95 (d, J=8.1, 1H), 7.73 (t, J=5.5, 1H), 7.51 (ddd, J=8.2, 6.8, 1.1, 1H), 7.45 (ddd, J=8.0, 6.9, 1.0, 1H), 3.66 (apt q, J=6.1, 2H), 2.82 (t, J=6.3, 2H), 2.66 (s, 3H), 2.35 (s, 3H), 1.81 (s, 1H). (ESI) m/z (M+H)+= 306.05.

Example 16

1-methyl-4-methylaminobenzo(g)imidazo(4,5-c)quinoline

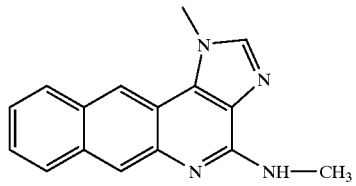

A mixture of 1-methyl-4-chlorobenzo(g)imidazo(4,5-c)quinoline (Preparation 19 in Example 11) (130 mg, 0.49 mmol) and MeNH$_2$ (2.0M/THF, 1.5 mL, 2.92 mmol) was heated in a pressure tube at 80° C. for 18 hours. After the reaction mixture was cooled to RT, it was diluted with EtOAc (100 mL), washed with sat'd NaCO$_3$ (50 mL), and brine. The organic layer was dried over MgSO$_4$, filtered and evaporated in vacuo. The crude material was submitted to flash chromatography (5% MeOH/EtOAc) affording the title compound as a pale white solid (5.2 mg, 4%). $^1$H NMR (CDCl$_3$): 8.44 (s, 1H), 8.35 (s, 1H), 7.94 (d, J=8.3, 1H), 7.90 (d, J=8.3, 1H), 7.72 (s, 1H), 7.46 (m, 1H), 7.40 (m, 1H), 5.95 (b, 1H), 4.28 (s, 3H), 3.31 (s, 3H). (ESI) m/z (M+H)+= 263.14. Inhibition of IKK-1 activity was measured using the assay of Example 2, where the inhibitory potential of the compound of Example 16 resulted in an IC$_{50}$ of 0.80 μM.

Example 17

1-methyl-4-(2-N-methylaminoethylamino)benzo(g)imidazo(4,5-c)quinoline

A solution of 1-methyl-4-chlorobenzo(g)imidazo(4,5-c)quinoline (Preparation 19 in Example 11) (130 mg, 0.49 mmol) in NH$_2$CH$_2$CH$_2$NH$_2$ (3.2 mL, 49 mmol), was heated at 60° C. for 18 hours. The solvent was evaporated in vacuo. The residue was diluted with EtOAc (50 mL) and washed with brine (20 mL). The organic layer was dried over MgSO$_4$, filtered, and concentrated. The crude material was submitted to flash chromatography (MeOH) affording the title compound as a pale white solid (6.9 mg, 5%). $^1$H NMR (CDCl$_3$): 8.52 (s, 1H), 8.33 (s, 1H), 7.96 (d, J=8.3, 1H), 7.94 (d, J=8.3, 1H), 7.77 (s, 1H), 7.46 (m, 1H), 7.42 (m, 1H), 6.22 (b, 1H), 4.36 (s, 3H), 3.85 (m, 2H), 3.10 (m, 2H), 1.60 (b, 1H). (ESI) m/z (M+H)+=292.18. Inhibition of IKK-1 activity was measured using the assay of Example 2, where the inhibitory potential of the compound of Example 17 resulted in an IC$_{50}$ of 1.0 μM.

Example 18

1-methyl-4-(2-hydroxyethylamino)benzo[g]imidazo[1,2-a]quinoxaline

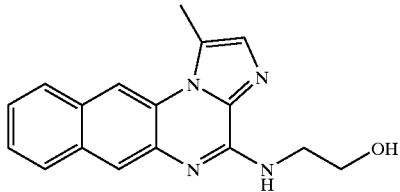

To a solution of 4-chloro-1-methylbenzo[g]imidazo[1,2-a]quinoxaline (0.060 g, 0.225 mmol) (Preparation 4 in Example 11) in 2 mL of THF was added 2-aminoethanol (0.11 mL, 1.80 mmol). The reaction tube was sealed and the mixture stirred at 80° C. for 16 hours. The resulting cooled mixture was then taken up in EtOAc, washed with water and brine, dried (Na$_2$SO$_4$) and evaporated. The resulting residue was recrystallized using i-PrOH to give Example 18 (0.062 g, 94%); mp 186–188° C.; IR (KBr, cm$^{-1}$) 3370, 3147, 1549, 1485, 1414; $^1$H NMR (DMSO-d6) 8.64 (s, 1H), 8.10–8.09 (m, 2H), 7.96 (d, J=7.5, 1H), 7.51–7.46 (m, 3H), 7.37 (s, 1H), 4.91 (t, J=5.2, 1H), 3.70–3.66 (m, 4H), 3.00 (s, 3H); MS (+ESI, M+H+) m/z 293; HPLC: 98.8% (230 nm). Inhibition of IKK-1 activity was measured using the assay of Example 2, where the inhibitory potential of the compound of Example 18 resulted in an IC$_{50}$ of 0.87•M.

Example 19

1-methyl-4-(2-piperidin-1-yl-ethylamino)benzo[g]imidazo[1,2-a]quinoxaline

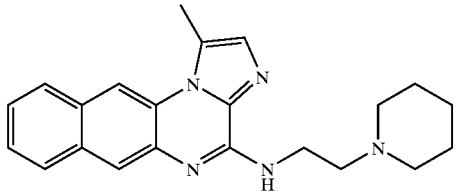

To a solution of 4-chloro-1-methylbenzo[g]imidazo[1,2-a]quinoxaline (0.055 g, 0.206 mmol) (Preparation 4 in Example 11) in of THF was added 1-(2-aminoethyl)piperidine (0.24 mL, 1.65 mmol). The reaction tube was sealed and the mixture stirred at 80° C. for 17 hours. The resulting cooled mixture was then taken up in EtOAc, washed with water and brine, dried (Na$_2$SO$_4$) and evaporated. The resulting residue was recrystallized using i-PrOH to give Example 19 (0.063 g, 84%); mp 170–172° C.; IR (KBr, cm$^{-1}$) 3300, 2932,1557,1483,1408; $^1$H NMR (DMSO-d6) 8.61 (s, 1H), 8.07–8.06 (m, 2H), 7.94 (d, J=7.6, 1H), 7.49–7.34 (m, 4H), 3.66 (br q, J=6.5, 2H), 2.97 (s, 3H), 2.59 (br t, J=6.5, 2H), 2.44 (br s, 4H), 1.54–1.39 (m, 6H); MS (+ESI, M+H+) m/z 360; HPLC: 97.6% (230 nm). Inhibition of IKK-1 activity was measured using the assay of Example 2, where the inhibitory potential of the compound of Example 19 resulted in an IC$_{50}$ of 1.7 μM.

The contents of all patents, patent applications, published PCT applications and articles, books, references, reference manuals and abstracts cited herein are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

What is claimed is:

1. A method of treating a condition selected from the group consisting of transplant rejection, rheumatoid arthritis, osteoarthritis, inflammatory bowel syndrome, asthma and chronic obstructive pulmonary disease (COPD) comprising administering to a mammal in need thereof, a theraneutically effective amount of a comnound having the formula

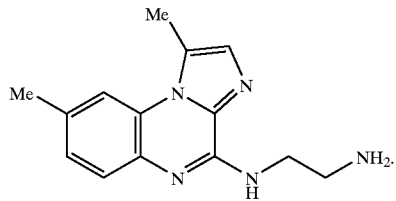

2. A method of treating a condition selected from the group consisting of transplant rejection, rheumatoid arthritis, osteoarthritis, inflammatory bowel syndrome, asthma and chronic obstructive pulmonary disease (COPD), comprising inhibiting IKK catalytic activity by administering to a mammal in need thereof, a compound having the formula

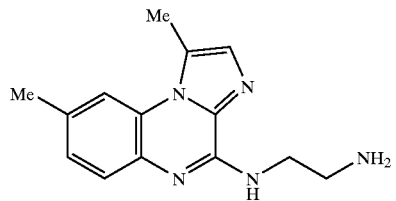

in an amount effective to inhibit IKK catalytic activity.

3. A method of treating a condition selected from the group consisting of transplant rejection, rheumatoid arthritis, osteoartbritis, inflammatory bowel syndrome, asthma and chronic obstructive pulmonary disease (COPD) comprising inhibiting phosphorylation of IκB by administering to a mammal in need thereof, a compound having the formula

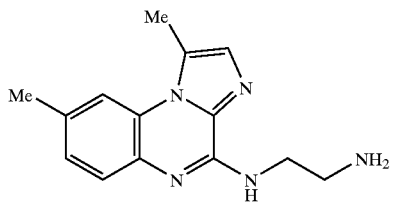

in an amount effective to inhibit phosphorylation of IκB.

4. A method of treating a condition selected from the group consisting of transplant rejection, rheumatoid arthritis, osteoarthritis, inflammatory bowel syndrome, asthma and chronic obstructive pulmonary disease (COPD) comprising administering to a mammal in need thereof, a compound having the formula

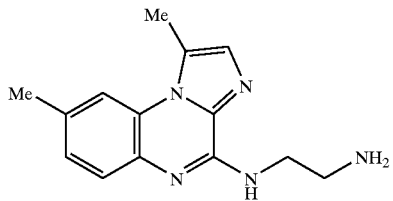

in an amount effective to inhibit IκB kinase (IKK), wherein IKK inhibition results in one or more of the following:

i) inhibition of IKK catalytic activity; or ii) inhibition of phosphorylation of IκB.

* * * * *